(12) United States Patent
Ogawa

(10) Patent No.: US 7,443,488 B2
(45) Date of Patent: Oct. 28, 2008

(54) ENDOSCOPE APPARATUS, METHOD OF OPERATING THE ENDOSCOPE APPARATUS, AND PROGRAM TO BE EXECUTED TO IMPLEMENT THE METHOD

(75) Inventor: Kiyotomi Ogawa, Tokyo (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 11/438,461

(22) Filed: May 22, 2006

(65) Prior Publication Data

US 2006/0268257 A1 Nov. 30, 2006

(30) Foreign Application Priority Data

May 24, 2005 (JP) ............................. P2005-151525

(51) Int. Cl.
*G01C 3/00* (2006.01)
(52) U.S. Cl. ...................................................... 356/3.13
(58) Field of Classification Search ....... 356/3.01–3.15, 356/4.01–4.1, 5.01–5.15
See application file for complete search history.

(56) References Cited

U.S. PATENT DOCUMENTS

| 6,009,189 | A | * | 12/1999 | Schaack | 382/154 |
| 6,059,718 | A | * | 5/2000 | Taniguchi et al. | 600/117 |
| 6,191,809 | B1 | * | 2/2001 | Hori et al. | 348/45 |

FOREIGN PATENT DOCUMENTS

| JP | 10-248806 | 9/1998 |
| JP | 2004-33487 | 2/2004 |
| JP | 2004-49638 | 2/2004 |

* cited by examiner

*Primary Examiner*—Thomas H. Tarcza
*Assistant Examiner*—Luke D Ratcliffe
(74) *Attorney, Agent, or Firm*—Ostrolenk, Faber, Gerb & Soffen, LLP

(57) ABSTRACT

An endoscope apparatus includes: an observation image capturing unit that captures an observation image of an object; a distance measuring unit that calculates an object distance from a distance measuring point, the calculation being made based on the observation image; and a display unit that displays the observation image and a set of information, the set of information being related to whether or not the object distance is within a measurable range.

38 Claims, 15 Drawing Sheets

ENDOSCOPE APPARATUS, METHOD OF OPERATING THE ENDOSCOPE APPARATUS, AND PROGRAM TO BE EXECUTED TO IMPLEMENT THE METHOD

BACKGROUND OF THE INVENTION

1. Field of the Invention

The present invention generally relates to an endoscope apparatus for a three dimensional measurement, a method of operating the endoscope apparatus and a program to be executed to implement the method. More specifically, the present invention relates to an endoscope apparatus that is adapted to display a distance to an object in real time, a method of operating the endoscope apparatus and a program to be executed to implement the method.

Priority is claimed on Japanese Patent Application No. 2005-151525, filed May 24, 2005, the content of which is incorporated herein by reference.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

In recent years, an endoscope has been widely used. The endoscope can observe organs in a body cavity while inserting a slender insertion portion into the body cavity. A medical instrument can also be inserted through a channel of the endoscope for medical operation. In the industrial fields, an industrial endoscope can be used for observing and checking damages and corrosions to boilers, turbines, engines As described above, an electronic endoscope has an insertion portion that further has a head portion that further includes an image pickup device such as a charge coupled device CCD. This electronic endoscope will hereinafter be referred to as an endoscope. An observed image is formed on the image pickup device. The observed image is then converted into an image signal by the image processing unit. The image signal is supplied to a monitor to display the image thereon.

Particularly, the industrial endoscope may be configured to be attached to or removed from a variety of optical adaptors for appropriate observations for checking or inspecting objects.

Japanese Unexamined Patent Application, First Publications, Nos. 2004-33487 and 2004-49638 disclose stereo optical adaptors that have a pair of right and left observation fields in observation optical systems.

SUMMARY OF THE INVENTION

In accordance with a first aspect of the present invention, a measuring endoscope apparatus may comprise: an electronic endoscope comprising an image pickup unit; an image processing unit that receives an image pickup signal from the image pickup unit, the image processing unit generating an image signal from the image pickup signal; a control unit comprising a measurement processing unit, the measurement processing unit receiving the image signal from the image processing unit, the measurement processing unit performing a measurement process based on the image signal; a display unit that receives an output image from the control unit, the display unit displaying the output image; an observation image capturing unit that captures an observation image of an object; a sight display unit that displays a sight at coordinates that are positioned on the observation image, the sight representing a distance measuring point, the sight being superimposed on the observation image; a distance measuring processing unit that calculates an object distance from the distance measuring point, the calculation being made based on the observation image by using the principle of triangulation; and an object distance information display unit that displays information of the first object distance.

Preferably, the measuring endoscope apparatus may further comprise: a sight position changing unit that changes a position of the sight; and a sight-coordinate setting unit that sets coordinates of the sight.

Preferably, the measuring endoscope apparatus may further comprises: a determination unit that determines whether or not the coordinates of the distance measuring point are within a measurable range; a distance measuring process control unit that inhibits starting a distance measuring process if the coordinates of the distance measuring point are outside the measurable range; and a measurable range display unit that displays the measurable range that is superimposed on the observation image.

Preferably, the object distance information display unit may display the information of the object distance that is superimposed on the observation image.

In accordance with a second aspect of the present invention, a program is provided to be executed for performing operations of an endoscope apparatus. The may comprise: an electronic endoscope comprising an image pickup unit; an image processing unit that receives an image pickup signal from the image pickup unit, the image processing unit generating an image signal from the image pickup signal; a control unit comprising a measurement processing unit, the measurement processing unit receiving the image signal from the image processing unit, the measurement processing unit performing a measurement process based on the image signal; a display unit that receives an output image from the control unit, the display unit displaying the output image. The program may comprise: capturing an observation image of an object; displaying a sight at coordinates that are positioned on the observation image, the sight representing a distance measuring point, the sight being superimposed on the observation image; calculating an object distance from the distance measuring point, the calculation being made based on the observation image by using the principle of triangulation; and displaying information of the first object distance.

Preferably, the program may further comprise: changing a position of the sight; and setting coordinates of the sight.

Preferably, the program may further comprise: determining whether or not the coordinates of the distance measuring point are within a measurable range; inhibiting starting a distance measuring process if the coordinates of the distance measuring point are outside the measurable range; and displaying the measurable range that is superimposed on the observation image.

Preferably, displaying information of the first object distance may comprise displaying the information of the object distance that is superimposed on the observation image.

In accordance with a third aspect of the present invention, an endoscope apparatus may comprise: an observation image capturing unit that captures an observation image of an object; a distance measuring unit that calculates an object distance from a distance measuring point, the calculation being made based on the observation image; and a display unit that displays the observation image and a set of information, the set of information being related to whether or not the object distance is within a measurable range.

Preferably, the endoscope apparatus may further comprise: a determination unit that determines whether or not the object distance is within the measurable range, the determination unit generating the set of information.

Preferably, the endoscope apparatus may further comprise: a sight display unit that displays at least one sight, the at least one sight being superimposed on the observation image, the at least one sight representing the distance measuring point.

Preferably, the sight display unit displays a plurality of sights on the observation image.

Preferably, the endoscope apparatus may further comprise: a sight position changing unit that changes a position of the at least one sight; and a sight-coordinate setting unit that sets coordinates of the at least one sight.

Preferably, the display unit displays an alert if the object distance is outside the measurable range.

Preferably, the measurable range is a three dimensional measurable range.

In accordance with a fourth aspect of the present invention, an endoscope apparatus comprises: an observation image capturing unit that captures an observation image of an object; a distance measuring unit that calculates an object distance from a distance measuring point, the calculation being made based on the observation image; and a determination unit that determines whether or not the object distance is within a measurable range.

Preferably, the endoscope apparatus may further comprise: a display unit that displays the observation image and a result of the determination of whether or not the object distance is within the measurable range.

Preferably, the endoscope apparatus may further comprise: a sight display unit that displays at least one sight, the at least one sight being superimposed on the observation image, the at least one sight representing the distance measuring point.

Preferably, the sight display unit displays a plurality of sights on the observation image.

Preferably, the endoscope apparatus may further comprise: a sight position changing unit that changes a position of the at least one sight; and a sight-coordinate setting unit that sets coordinates of the at least one sight.

Preferably, the display unit displays an alert if the object distance is outside the measurable range.

Preferably, the measurable range is a three dimensional measurable range.

In accordance with a fifth aspect of the present invention, a method of operating an endoscope apparatus may comprise: capturing an observation image of an object; calculating an object distance from a distance measuring point, the calculation being made based on the observation image; and displaying the observation image and a set of information, the set of information being related to whether or not the object distance is within a measurable range.

Preferably, the method may further comprise: determining whether or not the object distance is within the measurable range, the determination unit generating the set of information.

Preferably, the method may further comprise: displaying at least one sight, the at least one sight being superimposed on the observation image, the at least one sight representing the distance measuring point.

Preferably, displaying the at least one sight may comprise displaying a plurality of sights on the observation image.

Preferably, the method may further comprise: changing a position of the at least one sight; and setting coordinates of the at least one sight.

Preferably, the method may further comprise: displaying an alert if the object distance is outside the measurable range.

Preferably, the measurable range is a three dimensional measurable range.

In accordance with a sixth aspect of the present invention, a method of operating an endoscope apparatus may comprise: capturing an observation image of an object; calculating an object distance from a distance measuring point, the calculation being made based on the observation image; and determining whether or not the object distance is within a measurable range.

Preferably, the method may further comprise: displaying the observation image and a result of the determination of whether or not the object distance is within the measurable range.

Preferably, the method may further comprise: displaying at least one sight, the at least one sight being superimposed on the observation image, the at least one sight representing the distance measuring point.

Preferably, displaying the at least one sight may comprise displaying a plurality of sights on the observation image.

Preferably, the method may further comprise: changing a position of the at least one sight; and setting coordinates of the at least one sight.

Preferably, the method may further comprise: displaying an alert if the object distance is outside the measurable range.

Preferably, the measurable range is a three dimensional measurable range.

Objects, features, aspects, and advantages of the present invention will become apparent to those skilled in the art from the following detailed descriptions taken in conjunction with the accompanying drawings, illustrating the embodiments of the present invention.

BRIEF DESCRIPTION OF THE DRAWINGS

Referring now to the attached drawings which form a part of this original disclosure.

DETAILED DESCRIPTION OF THE INVENTION

Selected embodiments of the present invention will now be described with reference to the drawings. It will be apparent to those skilled in the art from this disclosure that the following descriptions of the embodiments of the present invention are provided for illustration only and not for the purpose of limiting the invention as defined by the appended claims and their equivalents.

First Embodiment

Figure 1:
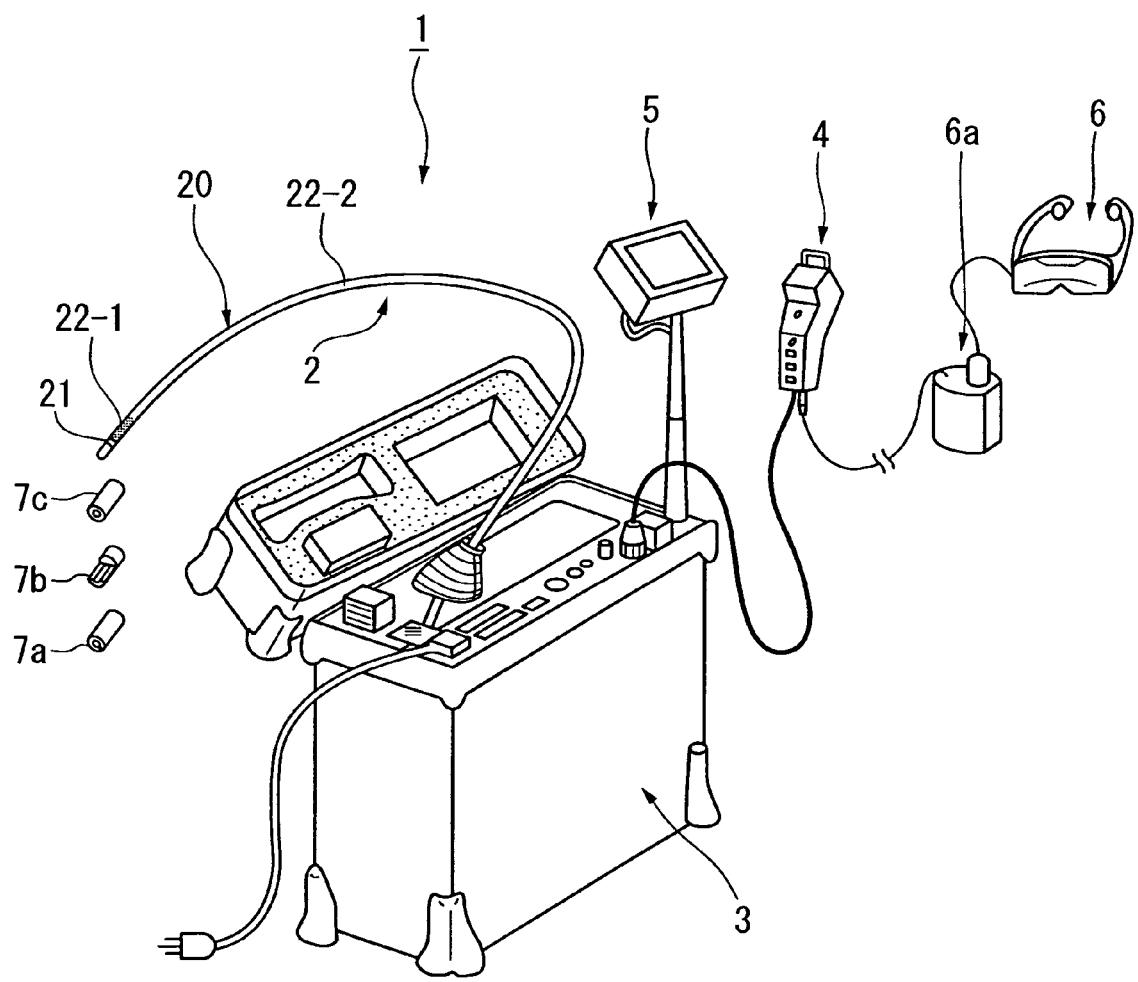
FIG. 1 is a schematically perspective view illustrating an entire configuration of an endoscope apparatus in accordance with a first embodiment of the present invention.

FIG. 1 is a schematically perspective view illustrating an entire configuration of an endoscope apparatus in accordance with a first embodiment of the present invention. An endoscope apparatus 1 may include, but is not limited to, an endoscope 2, a control device 3, a remote controller 4, a main display 5, a face mount display 6, and a face mount display adaptor 6a. The endoscope 2 includes an insertion portion 20. The control device 3 controls the endoscope apparatus 1. The control device 3 may include a container that contains the insertion portion 20 of the endoscope 2. The remote controller 4 is functionally coupled to the control device 3. The remote controller 4 is operated to render the control device 3 control the endoscope apparatus 1.

The main display 5 is adapted to display an image that is captured by the endoscope 2. The main display 5 is functionally coupled to the control device 3. The main display 5 is adapted to display the contents of operation and/or control to the endoscope apparatus 1. Typical examples of the contents of operation and/or control may include a menu of processes. The main display 5 can be realized by a liquid crystal display that may hereinafter be referred to as LCD.

The face mount display 6 may hereinafter be referred to as FMD. The FMD 6 may be adapted to display a natural or original image that is originally captured by the endoscope 2 and/or an artificial image that is produced from the natural or original image. The artificial image may include, but is not limited to, a stereoscopic or three dimensional image. The face mount display adaptor 6a is functionally coupled to the remote controller 4 or the control device 3 as well as functionally coupled to the FMD 6. The face mount display adaptor 6a is configured to receive image data from the remote controller 4 or the control device 3. The face mount display adaptor 6a is configured to supply the image data to the FMD 6.

The insertion portion 20 includes a head portion 21, a curving portion 22-1, and a flexible tube portion 22-2. The head portion 21 is mechanically coupled to a first end of the flexible tube portion 22-2. The head portion 21 has a rigidity. The flexible tube portion 22-2 has a flexibility. The flexible tube portion 22-2 is allowed to be curved passively. The curving portion 22-1 extends between the head portion 21 and the flexible tube portion 22-2. The curving portion 22-1 contains a curving mechanism that actively curves the curving portion 22-1 so as to actively move the head portion 21. The curving mechanism is not illustrated. The head portion 21 is configured to allow an optical adaptor to be attachable to and removable from the head portion 21. Typical examples of the optical adaptor may include, but are not limited to, a pair of stereo optical adaptors 7a, 7b that provide two observation fields, and a normal optical adaptor 7c that provides a single observation field.

Figure 2:
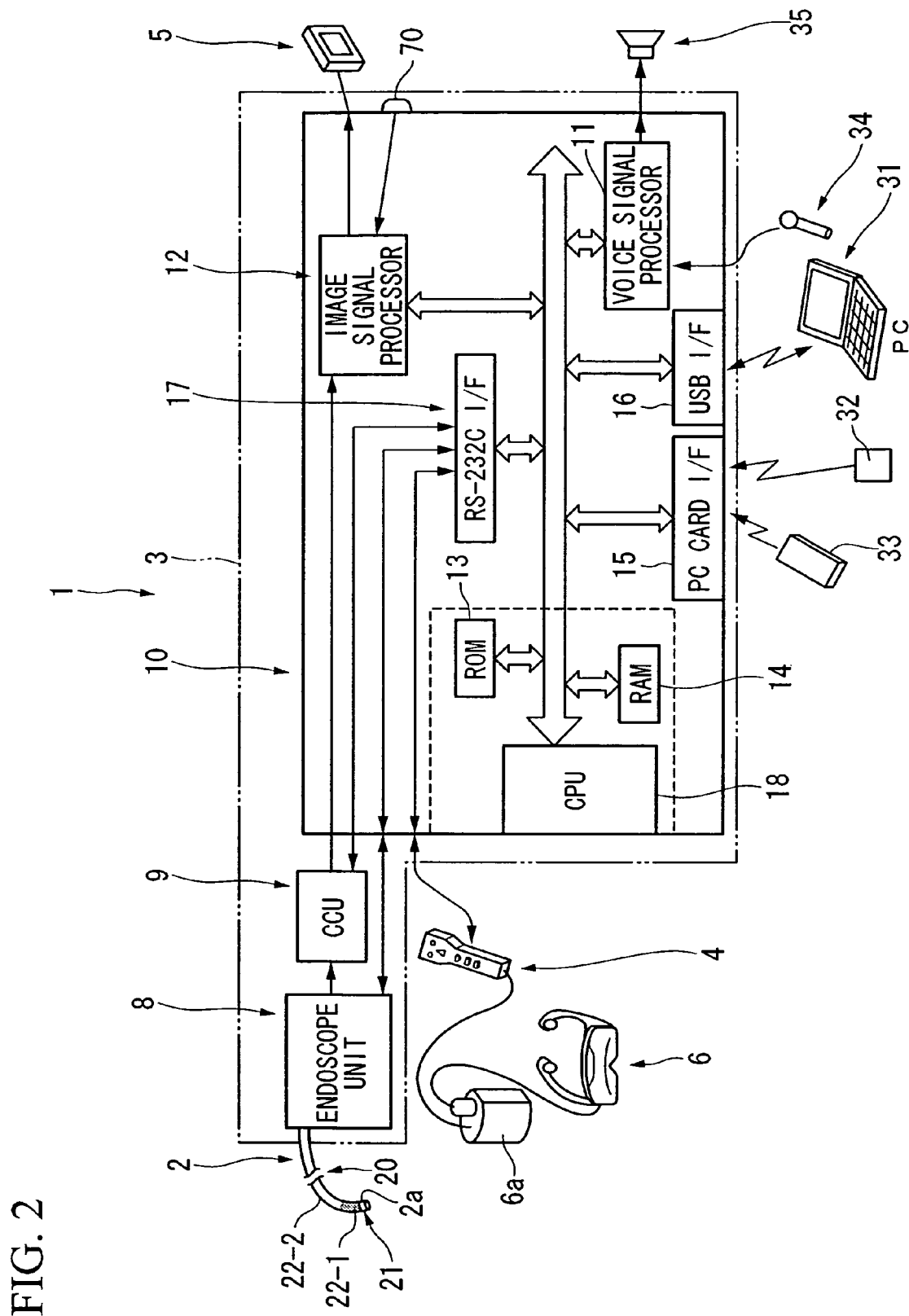
FIG. 2 is a block diagram illustrating a configuration of a control device shown in FIG. 1.

FIG. 2 is a block diagram illustrating a configuration of the control device 3 shown in FIG. 1. The control device 3 may include, but is not limited to, an endoscope unit 8, an image processing unit 9, and a control unit 10. The image processing unit 9 can be realized by a camera control unit that may hereinafter be referred to as CCU. The endoscope unit 8 is connected to a second end of the insertion portion 20. The second end of the insertion portion 20 is distal to the head portion 21. The first end of the insertion portion 20 is proximal to the head portion 21. The endoscope unit 8 may include, but is not limited to, a light source as an illuminator that supplies an illumination for observation, and a curving device that controls the curving mechanism contained in the curving portion 22-1 that curves the curving portion 22-1 for observation. The head portion of the insertion portion 20 integrates a solid state image pickup device 2a.

The image processing unit 9 is adapted to receive a captured signal from the solid state image pickup device 2a. The image processing unit 9 is also adapted to transform or convert the captured signal into an image signal such as an NTSC signal. The image processing unit 9 is further adapted to supply the image signal to the control unit 10.

The control unit 10 may include, but is not limited to, a voice signal processing circuit 11, an image signal processing circuit 12, a ROM 13, a RAM 14, a PC card interface 15, an USB interface 16, an RS-232C interface 17, and a CPU 18. The PC card interface 15 may hereinafter be referred to as a PC card I/F 15. The USB interface 16 may hereinafter be referred to as an USB I/F 16. The RS-232C interface 17 may hereinafter be referred to as an RS-232C I/F 17. The CPU 18 executes a main program to render the voice signal processing circuit 11, the image signal processing circuit 12, the ROM 13, the RAM 14, the PC card I/F 15, the USB I/F 16, and the RS-232C I/F 17 perform predetermined functions assigned thereto.

The RS-232C I/F 17 is connected to image processing unit 9 as the CCU, the endoscope unit 8, and the remote controller 4. The remote controller 4 controls the endoscope unit 8 and the image processing unit 9 and provides operating instructions to the endoscope unit 8 and the image processing unit 9. The RS-232C I/F 17 is configured to communicate with the voice signal processing circuit 11, the image signal processing circuit 12, the ROM 13, the RAM 14, the PC card I/F 15, and the USB I/F 16, in order to control and/or operate the endoscope unit 8. The communication is made based on operations of the remote controller 4.

The USB I/F 16 is an interface that electrically connects the control device 3 to an external device 31 that is typically represented by a personal computer. The USB I/F 16 enables the external device 31 to send a variety of external instructions to the control device 3. Typical examples of the external instructions may include, but are not limited to, instructions to display an image captured by the endoscope 2, and instructions to process image data for measurement operations. The USB I/F 16 also transfers control information and data between the external device 31 and the control device 3, wherein the control information and data need to be used to perform predetermined processes or functions.

The PC card I/F 15 is configured to allow an external storage medium to be attached to and removed from the PC card I/F 15. Typical examples of the external storage medium may include, but are not limited to, a PCMCIA memory card 32 and a compact flash (registered trademark) memory card 33. The external storage medium is 15 attached to the PC card I/F 15 so as to enable the control device 3 to obtain or capture a set of data related to control processes and another set of data related to an image that are stored in the external storage medium, and also enable the control device 3 to store the above sets of data in the external storage medium.

The image signal processing circuit 12 is configured to receive, from the image 20 processing unit 9, an image that has been captured by the endoscope 2. The image signal processing circuit 12 is also configured to synthesize the image with a graphic operation menu to generate a synthesized image. The image signal processing circuit 12 is further configured to receive the image signal from the image processing unit 9, and to receive a display signal from the CPU 18. The display signal is generated with 25 reference to an operation menu that is further generated under the control by the CPU 18. The image signal processing circuit 12 is furthermore configured to synthesize the image signal with the display signal to generate a synthesized signal. The image signal processing circuit 12 may additionally be configured to apply additional processes to the synthesized image and the synthesized signal. The additional processes need to display on a screen of the LCD 5. The image signal processing circuit 12 is configured to supply the additionally processed image and signal to the LCD 5. The image signal processing circuit 12 may also be configured to perform processes for displaying solely the image or the operation menu. In a case, the image and the operation menu may be separately displayed on the screen of the LCD 5. In another case, the synthesized image including the image captured by the endoscope 2 and the operation menu may be displayed on the screen of the LCD 5.

The voice signal processing circuit 11 is configured to receive a voice signal from the outside. Typical examples of the voice signal may include, but are not limited to, a type of voice signal that is generated by a microphone 34 and should be stored in a storage medium such as a memory card, another type of voice signal that is generated by replaying the storage medium such as the memory card, and still another type of voice signal that is generated by the CPU 18. The voice signal processing circuit 11 is configured to apply processes to the voice signal, wherein the processes need to replay the voice signal. A typical example of the voice signal may include, but is not limited to, an amplification of the voice signal. The voice signal processing circuit 11 is configured to supply the processed voice signal to a speaker 35 that is provided outside the control device 3. The speaker 35 speaks a voice based on the voice signal.

The CPU 18 executes a program that is stored in the ROM 13 to render the voice signal processing circuit 11, the image signal processing circuit 12, the ROM 13, the RAM 14, the PC card I/F 15, the USB I/F 16, and the RS-232C I/F 17 perform predetermined functions assigned thereto. The execution of the program renders the control device 3 control the endoscope apparatus 1.

Figure 3:
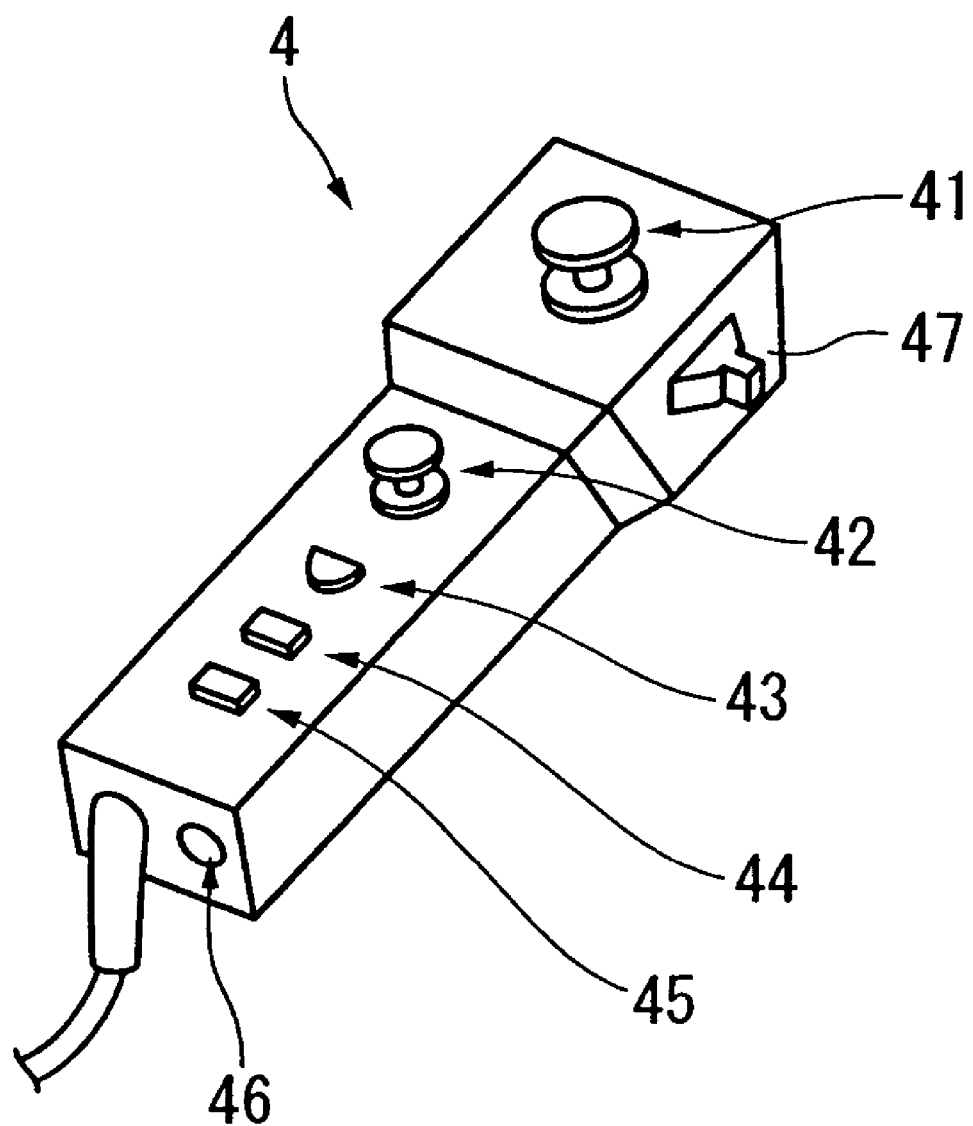
FIG. 3 is a schematically perspective view illustrating the remote controller 4 shown in FIG. 1.

FIG. 3 is a schematically perspective view illustrating the remote controller 4 shown in FIG. 1. The remote controller 4 may include, but is not limited to, a joy stick 41, a lever switch 42, a freeze switch 43, a store switch 44, a measuring execution switch 45, a connector 46, and a zoom lever 47.

The joy stick 41 is a switch that is configured to generate instructions to render the flexible tube portion 22-2 exhibit a curving motion. Operations to tilt the joy stick 41 renders the flexible tube portion 22-2 exhibit a curving motion. The curving motion of the flexible tube portion 22-2 is defined by a direction toward which the flexible tube portion 22-2 curves, and a magnitude by which the flexible tube portion 22-2 curves. The direction of the curving motion depends on a direction toward which the joy stick 41 tilts. The magnitude of the curving motion depends on a magnitude by which the joy stick 41 tilts.

The lever switch 42 is a switch that is used to operate graphically displayed menus and to move a pointer for measurement operation. The lever switch 42 is configured to be tilted to operate the menu and to move the pointer. The freeze switch 43 is a switch that is operated to control the display operation by the LCD 5. Operating the freeze switch 43 freezes the image that is being displayed by the LCD 5. The store switch 44 is used to store the frozen image in a memory card, wherein the frozen image has been obtained by freezing the image with operating the freeze switch 43. The measuring execution switch 45 is used to execute a software for measuring operations. The freeze switch 43, the store switch 44 and the measuring execution switch 45 may be configured to be pushed down to switch ON and OFF.

The connector 46 may be adapted to be connected with an electric cable that electrically connects the remote controller 4 to the FMD 6. A stereo observation can be made using the FMD 6. The zoom lever 47 is a directional switch that may be configured to tilt in one dimensional direction to control electric zooming. Operation to tilt the zoom level 47 in one direction makes an electronic image magnified or larger. Another operation to tilt the zoom level 47 in the opposite direction makes the electronic image reduced or smaller.

Figure 4:
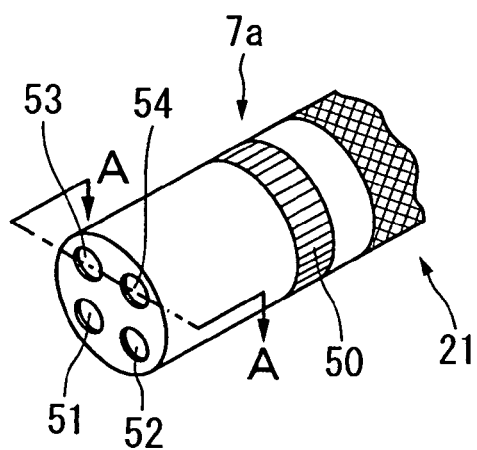
FIG. 4 is a schematic perspective view illustrating a stereo optical adaptor shown in FIG. 1.
Figure 5:
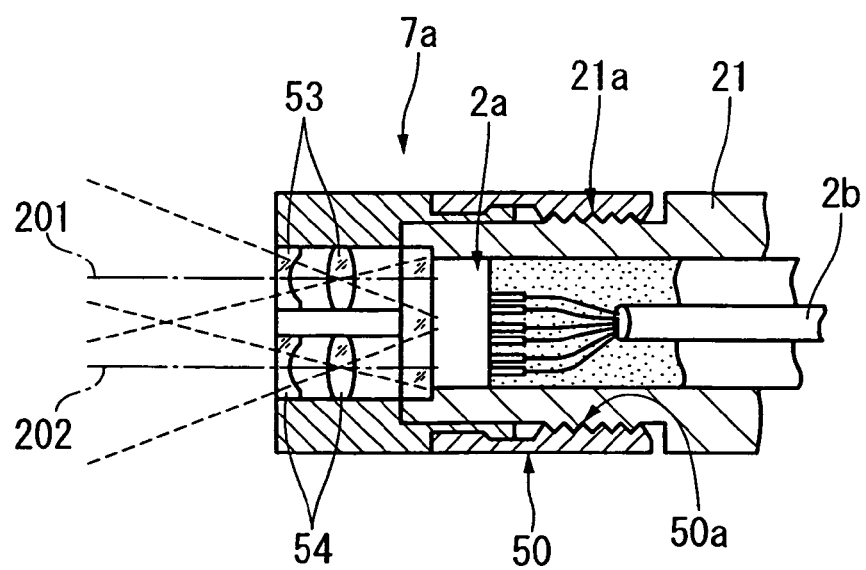
FIG. 5 is a fragmentary cross sectional view illustrating the stereo optical adaptor taken along an A-A line of FIG. 4.

FIG. 4 is a schematic perspective view illustrating a stereo optical adaptor 7a shown in FIG. 1. FIG. 5 is a fragmentary cross sectional view illustrating the stereo optical adaptor 7a, taken along an A-A line of FIG. 4. The stereo optical adaptor 7a is adapted to obtain a direct vision. The stereo optical adaptor 7a may include a pair of illumination lenses 51, 52 and two objective lens systems 53 and 54. As shown in FIG. 5, the stereo optical adaptor 7a is fixed to the head portion 21 of the endoscope 2 by a fixing ring 50. The head portion 21 has a male screw 21a. The fixing ring 50 has a female screw 50a. The female screw 50a of the fixing ring 50 is bolted with the male screw 21a of the head portion 21 so that the stereo optical adaptor 7a fixed to the head portion 21.

As shown in FIG. 5, the head portion 21 includes the solid state image pickup device 2a. The solid state image pickup device 2a is connected with a signal line 2b so that the solid state image pickup device 2a is electrically connected to the endoscope unit 8 through the signal line 2b. The two objective lens systems 53 and 54 have optical axes 201 and 202, respectively. The two objective lens systems 53 and 54 are configured to form two optical images on an image pickup surface of the solid state image pickup device 2a. The optical images are optoelectric-converted into image pickup signals by the solid state image pickup device 2a. The image pickup signals are supplied through the signal line 2b and the endoscope unit 8 to the image processing unit 9. The image pickup signals are then converted into an image signal by the image processing unit 9. The image signal is supplied to the image signal processing circuit 12.

The endoscope apparatus 1 may be adapted to measure five types of optical data (a1), (a2), (b), (c), and (d) related to the image pickup optical system. The five types of optical data (a1), (a2), (b), (c), and (d) are unique to the endoscope 2. The endoscope apparatus 1 may also be adapted to store the measured five types of optical data (a1), (a2), (b), (c), and (d) in a storage medium, for example, memory cards such as the PCMCIA memory card 31 and the compact flat memory card 33.

Examples of the five types of unique optical data may include the first to fifth types of optical data. The first type of optical data (a1) is a geometrical distortion correction table of two objective optical systems. The second type of optical data (a2) is another geometrical distortion correction table of image transmission optical systems. The third type of optical data (b) is respective focusing distances of two image forming optical systems. The fourth type of optical data (c) is a distance between principal points of the two image forming optical systems. The fifth type of optical data (d) is position coordinates on the images of the two image forming optical systems, wherein the position coordinates are aligned to the optical axes of the two image forming optical systems.

After the endoscope apparatus 1 has obtained the above unique five types of optical data (a1), (a2), (b), (c), and (d), the external device 31 such as a personal computer can be connected to the endoscope apparatus 1 so as to perform the following first to fifth processes.

The first process is to read out the above unique five types of optical data (a1), (a2), (b), (c), and (d) from the above memory card.

The second process is to make the endoscope 2 to capture an image of an object that is to be measured.

The third process is to perform a transformation of coordinates that belong to the captured image, the transformation being made with reference to the above unique five types of optical data (a1), (a2), (b), (c), and (d) so as to generate a coordinate-transformed image on the transformed coordinates.

The fourth process is to find three dimensional coordinates of a point by matching the captured image data to the coordinate-transformed image.

The fifth process is to perform a variety of three dimensional measurements based on the above three dimensional coordinates.

The endoscope apparatus 1 may be also adapted to display in real time a distance of a camera from an object on a live display screen. An operator or user can recognizes the current distance of the camera from the object by viewing the displayed distance on the live display screen, even it is difficult for the operator to directly view and recognize an actual positional relationship between the camera and the object.

Figure 6:
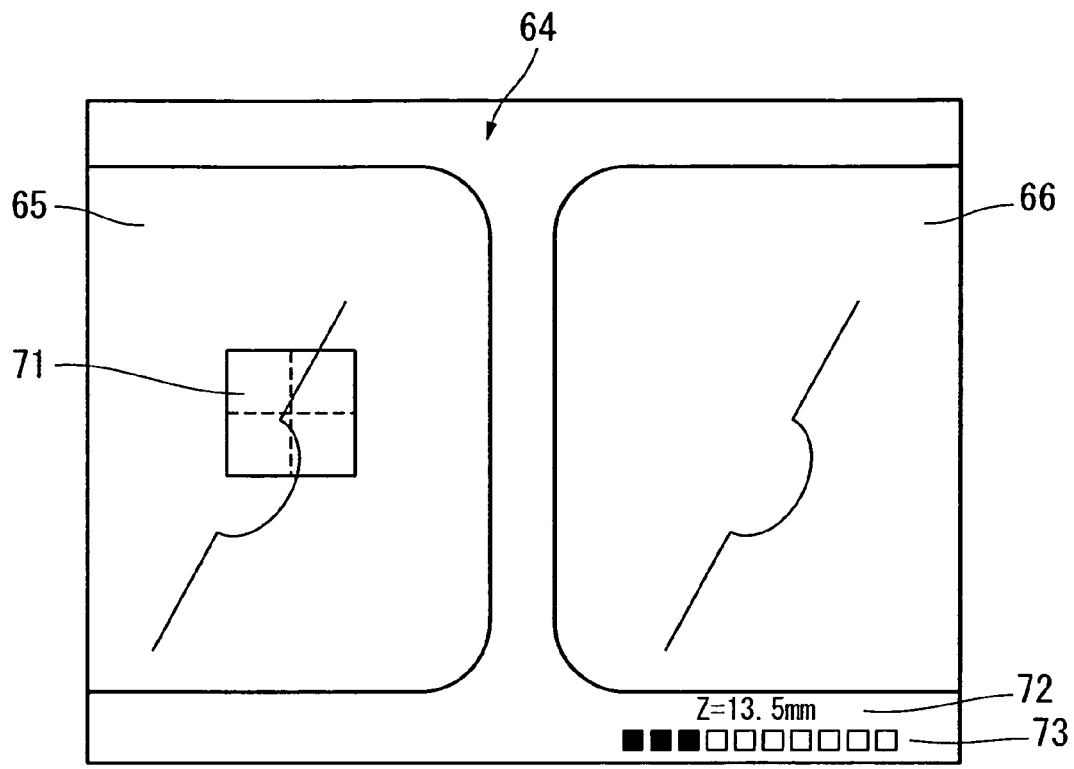
FIG. 6 is a view illustrating first and second images that are displayed on a screen of the main display shown in FIG. 1.

FIG. 6 is a view illustrating first and second images 65 and 66 that are displayed on a screen 64 of the LCD 5 shown in FIG. 1. The first image 65 is superimposed with a sight 71. The second image 66 is free of the sight 71. The sight 71 is used as a distance measuring point to measure, in real time, a distance to the distance measuring point. The measured distance to the distance measuring point is displayed as a distance-representing character 72 on the screen 64, wherein the distance-representing character 72 represents the distance. The measured distance to the distance measuring point is further graphically displayed as a distance-representing bar graph 73 on the screen 64.

Figure 7:
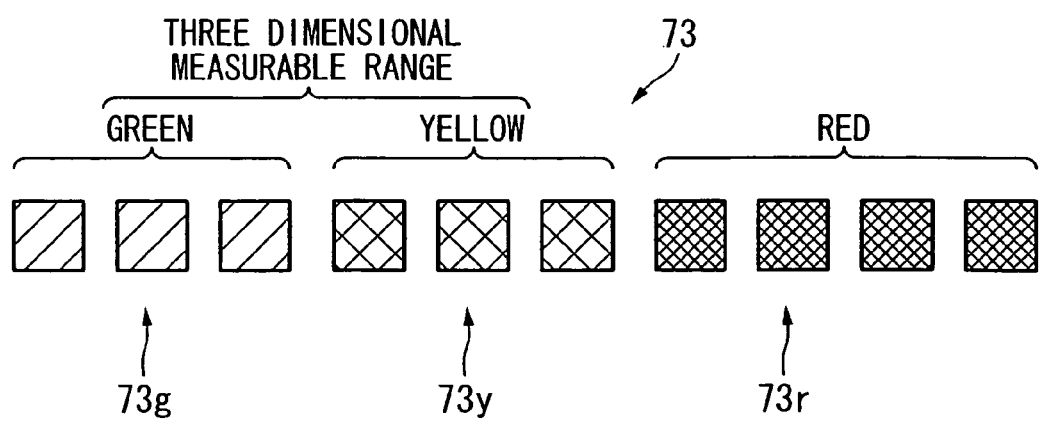
FIG. 7 is a view illustrating the distance-representing bar graph shown in FIG. 6.

FIG. 7 is a view illustrating the distance-representing bar graph 73 shown in FIG. 6. The distance-representing bar graph 73 includes a green bar graph 73g, a yellow bar graph 73y, and a red bar graph 73r. The green bar graph 73g represents that a highly accurate three dimensional measurement is available. The yellow bar graph 73y represents that an average-accurate three dimensional measurement is available. The red bar graph 73r represents that no satisfactory three dimensional measurement is available. The green and yellow bar graphs 73g and 73y represent that the measured distance is within the three dimensional measurable range.

The endoscope apparatus 1 is adapted to display, in read time, the distance to the object along with the live image on the display screen. An operator is permitted to confirm the distance to the object and to determine whether or not the highly accurate three dimensional image is obtainable. Namely, the operator is permitted to switch the measurement mode into the three dimensional measurement mode, after the camera becomes closer to the object so that the highly accurate three dimensional measurement is available.

Process for displaying the distance to the object along with the live image on the screen will be described in details.

Figure 20:
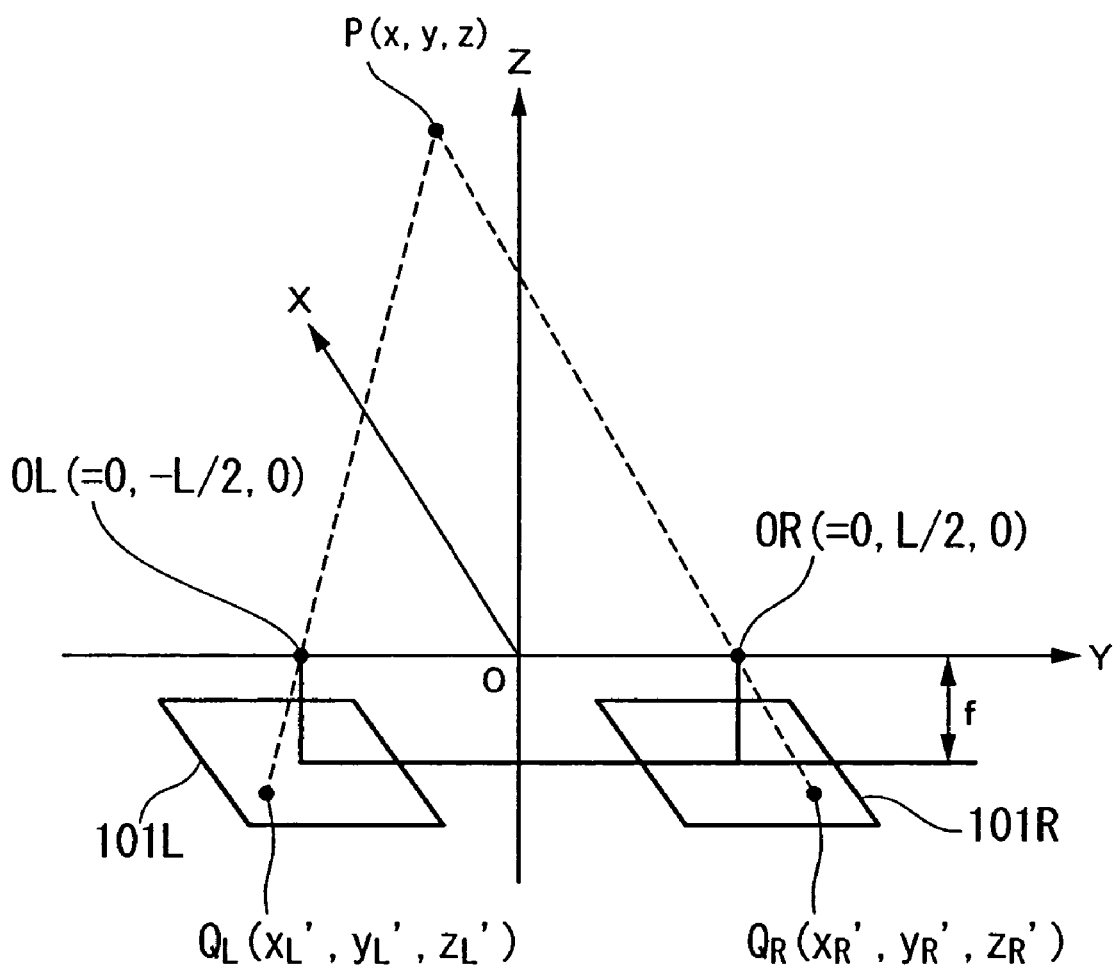
FIG. 20 is a view illustrating a positional relationship between paired first and second images on a three dimensional coordinate system with x-axis, y-axis, and z-axis.

A pair of the stereo optical adaptors provides a pair of observation fields. The pair of the stereo optical adaptors is used to determine three dimensional space coordinates of an object by using the principle of triangulation. The determination is made based on a pair of optical coordinates that belong to a pair of optical systems that capture an object image. FIG. 20 is a view illustrating a positional relationship between paired first and second images on a three dimensional coordinate system with x-axis, y-axis, and z-axis. A distance measuring point P is subject to the measurement. The image pickup device has first and second image forming surfaces 101L and 101R. An image of the distance measuring point P is formed on the first and second image forming surfaces 101L and 101R. An optical system has first and second principal points OL and OR. A distance f is a focal length. Points $Q_L$ and $Q_R$ are first and second focusing points of the distance measuring point P, respectively. A length L is defined to be a distance between the first and second principal points OL and OR. The following equation (1) is established from a straight line that is defined between the second focusing point $Q_R$ and the second principal point OR.

$$x/x_R = \{y-(L/2)\}/\{y_R-(L/2)\} = z/(-f) \qquad (1)$$

The following equation (2) is also established from another straight line that is defined between the first focusing point $Q_L$ and the first principal point OL.

$$x/x_L = \{y+(L/2)\}/\{y_L-(L/2)\} = z/(-f) \qquad (2)$$

The above equations (1) and (2) are solved for x, y, and z, to determine three dimensional coordinates of the distance measuring point P. A distance to the object can be determined based on the three dimensional coordinates of the distance measuring point P.

The distance or length L between the first and second principal points OL and OR and the focusing points of the optical system have previously been recorded as optical data. Coordinates of the first focusing point $Q_L$ are coordinates of the sight 71 that is the distance measuring point. The sight 71 is superimposed with the first image 65. The second focusing point $Q_R$ can be obtained by finding a point corresponding to the distance measuring point P from the second image 66.

The first focusing point $Q_L$ included in the first image 65 corresponds to the second focusing point $Q_R$ included in the second image 66. When the first image 65 is set as the reference image, the second focusing point $Q_R$ is found from the second image 66 by the matching process so that the second focusing point $Q_R$ corresponds to the first focusing point $Q_L$. Space coordinates of the second focusing point $Q_R$ included in the second image 66 are calculated by using the above equations (1) and (2). A distance to the distance measuring point can be found based on the calculated space coordinates.

In the above case, the first image 65 is set as the reference image and the sight 71 is superimposed with the first image 65. It is possible for the second image 66 to be set as the reference image that is superimposed with the sight 71.

The endoscope apparatus 1 is adapted to display the distance to an object in real time on a screen of a display together with the live image. An operator can recognize or confirm the distance to the object in order to determine whether the highly accurate three dimensional measurement is available. Namely, the operator can switch the measuring mode into the three dimensional measuring mode after the camera comes close to the object so as to obtain the highly accurate three dimensional image.

Figure 10:
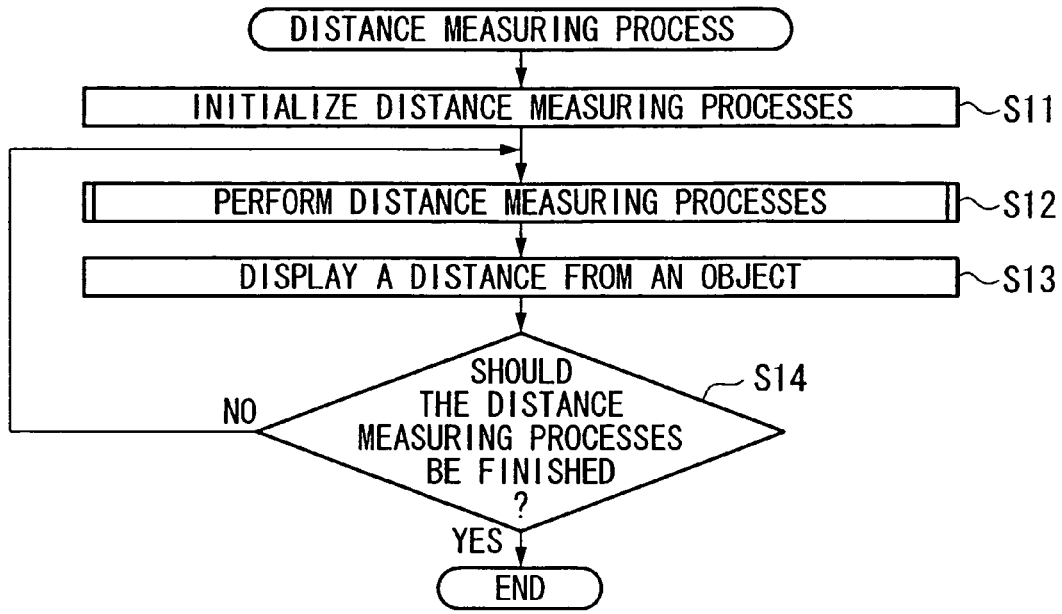
FIG. 10 is a flow chart illustrating processes of the distance measuring and displaying, in real time, a distance from the distance measuring point on the main display device shown in FIG. 1.

FIG. 10 is a flow chart illustrating processes for displaying, in real time, a distance from the distance measuring point on the LCD 5 shown in FIG. 1.

An initialization process is made in Step S11 prior to performing a distance measuring function. The distance measuring function is started by operating the zoom lever 47 provided that the following start conditions are satisfied.

The first condition is that the optical adaptor is set as the stereo optical adaptor.

The second condition is that the LCD 5 is currently displaying the live image or the freeze image.

The third condition is that the electronic zoom is a wide edge or one time magnification.

In parallel to displaying the live image or the freeze image, the distance
measuring process is performed in Step S12 of FIG. 10.

Figure 11:
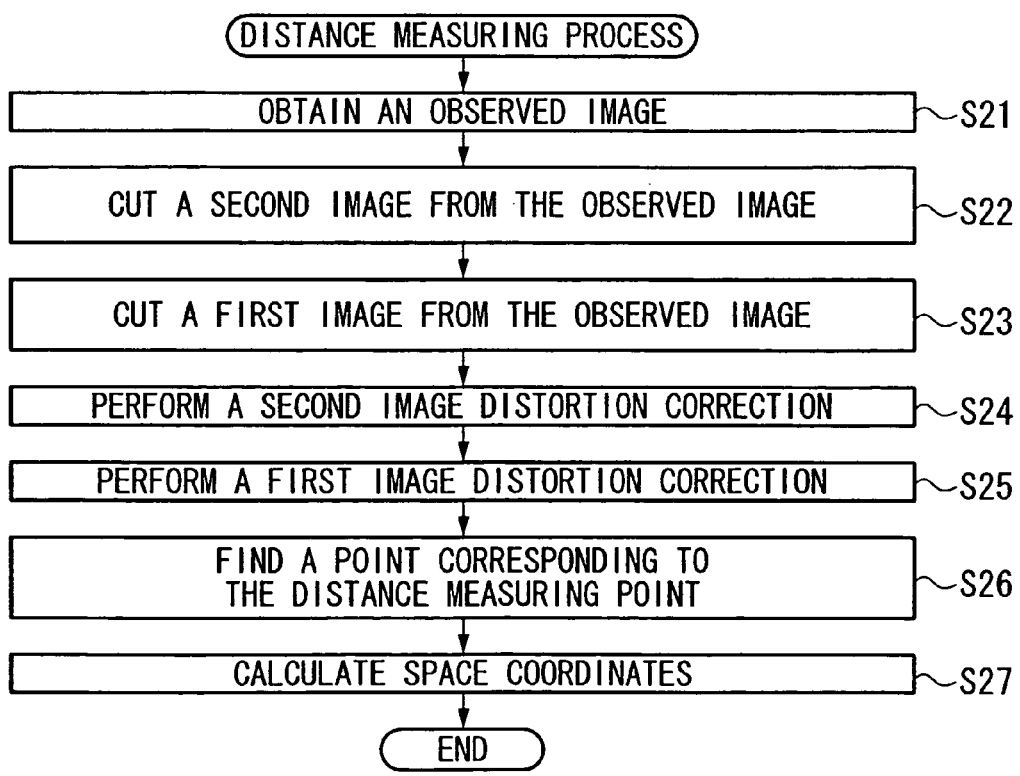
FIG. 11 is a flow chart illustrating distance measuring processes of Step S12 shown in FIG. 10.

FIG. 11 is a flow chart illustrating distance measuring processes of Step S12 shown in FIG. 10. The distance measuring process of Step S12 includes processes shown in FIG 11. In Step S21, an observed image is obtained. The obtained image is then developed on a memory. In Step S22, the second image 66 is cut from the observed image. In Step S23, the first image 65 is cut from the observed image.

In Step S24, a correction is made to a distortion of the second image 66. In Step S25, another correction is made to another distortion of the first image 65. In general, an image obtained by a lens system has an optical distortion. This distortion may cause a large error in accuracy of the measurement. In Steps S24 and S25, coordinate conversions are made to remove the distortions from the first and second images 65 and 66. The corrections to the distortions are made using the optical data that are stored in the memory card.

In Step S26, a point corresponding to the distance measuring point is found. Namely, as shown in FIG. 6, the first image 65 is superimposed with the sight 71. The distance measuring point is set at a center point of the sight 71, thereby forming a template. A pattern matching process is performed using the template so that a correlation between the first and second images 65 and 66 is found. A point corresponding to the distance measuring point is found from the second image 66 with reference to the correlation.

In Step S27, space coordinates are calculated using the above equations (1) and (2) based on the principle of triangulation so that a distance to the distance measuring point is found using the calculated space coordinates. The distance or length L between the first and second principal points OL and OR of the optical system and the focal length thereof have previously been recorded as optical data in the memory card. Coordinates of the first focusing point $Q_L$ are coordinates of the sight 71 that is the distance measuring point. In Step S26, the second focusing point $Q_R$ can be obtained by finding a point corresponding to the distance measuring point from the second image 66.

After the distance measuring process is performed in Step S12 of FIG. 10 that comprises the processes of Steps S21 through S27 shown in FIG. 11, then the process flow will enter into Step S13, in which the distance to the distance measuring point is displayed on the screen 64 of the LCD 5. Namely, as shown in FIG. 6, the distance to the object is displayed as the distance-representing character 72 on the screen 64. The distance to the object is also displayed as the distance-representing bar graph 73 on the screen 64.

As shown in FIG. 7, the distance-representing bar graph 73 includes the green bar graph 73g, the yellow bar graph 73y, and the red bar graph 73r. The range of distance that permits the highly accurate three dimensional measurement depends on the characteristics of the optical adaptor. The lengths of the green, yellow and red bar graphs, 73g, 73y and 73r and the value of each bar graph may be set based on the optical characteristics of the optical adaptor, wherein the optical characteristics of the optical adaptor have been stored in the memory card.

In Step S14, a determination is made of whether a distance measuring display finishing operation has been performed. If the distance measuring display finishing operation has not yet been performed, then the process flow will return to the above Step S12, and the distance measuring process will continue. The distance to the object is displayed in real time together with the live image or the freeze image. If the distance measuring display finishing operation has been performed, then the distance measuring process has been completed and finished.

Figure 8:
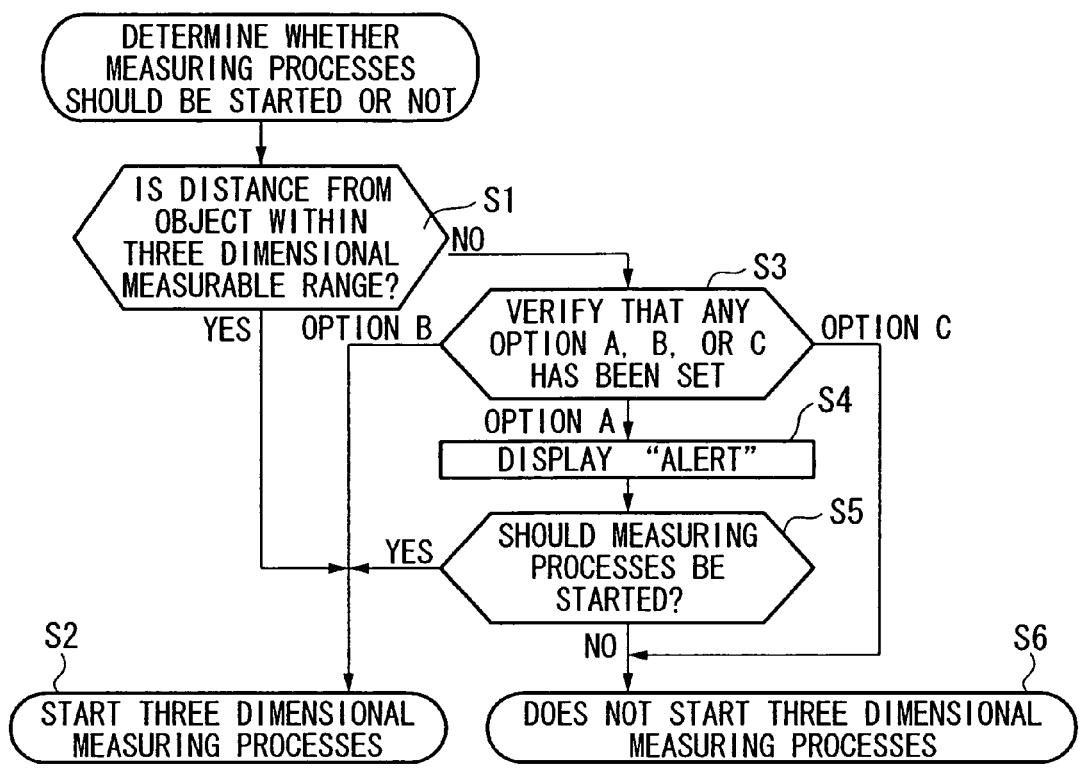
FIG. 8 is a flow chart illustrating a determination process prior to starting the three dimensional measuring process for measuring the dimension of an object.
Figure 9A:
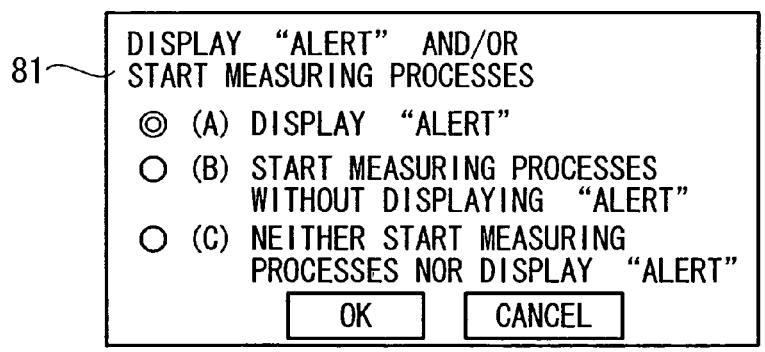
FIG. 9A is a view illustrating examples of a set of alert options, one of which is selected prior to starting the measuring process.
Figure 9B:
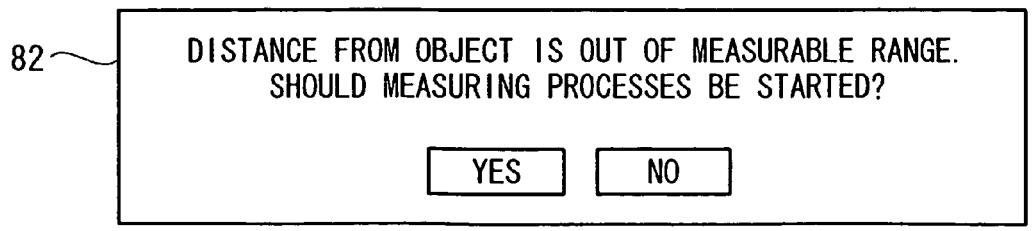
FIG. 9B is a view illustrating an example of a query of whether the measuring process starts or not.

The following descriptions will be directed to processes for determining whether or not the three dimensional measurement process should be performed, the determination being made based on the result of the distance measuring process. FIG. 8 is a flow chart illustrating a determination process prior to starting the three dimensional measuring process for measuring the distance to an object. FIG. 9A is a view illustrating examples of a set of alert options, one of which is selected prior to starting the measuring process. FIG. 9B is a view illustrating an example of a query of whether the measuring process starts or not.

In Step S1, it is determined whether an object distance of an object is within a three dimensional measurable range. If the distance is within the three dimensional measurable range, then the process flow will enter into Step S2, in which the measuring process starts. If the distance is out the three dimensional measurable range, then the process flow will enter into Step S3, where which one of the predetermined alert options has been set prior to starting the measuring process. In Step S3, a set of alert options 81 is displayed prior to starting the measuring process so as to permit an operator to select one of the predetermined alert options displayed.

Typical examples of the predetermined alert options may include, but are not limited to, the following three alert options.

(A) display "alert";
(B) start the measuring process without displaying "alert"; and
(C) do not start the measuring process without displaying "alert".

When the alert option (A) "display alert" is selected in Step S3, the process flow will enter into Step S4, in which a query is made of whether the measuring process starts or not. Namely, a display is made that the distance to the object is out the three dimensional measurable range and thus a query 82 is made of whether the measuring process starts or not. An operator is permitted to determine whether the measuring process starts or not even the distance to the object is out the three dimensional measurable range.

In Step S5, the operator's determination on whether the measuring process starts or not is confirmed. If the determination that the measuring process starts is confirmed, then the process flow will enter into Step S2, in which the measuring process is started. If the determination that the measuring process does not start is confirmed, then the process flow will enter into Step S6, in which the process for preparing the measuring process is discontinued.

When the alert option (B) "starts the measuring process without displaying alert" is selected in Step S3, the process flow will enter into Step S2, in which the measuring process is started.

When the alert option (C) "do not start the measuring process without displaying alert" is selected in Step S3, the process flow will enter into Step S6, in which the process for preparing the measuring process is discontinued.

Second Embodiment

Figure 12:
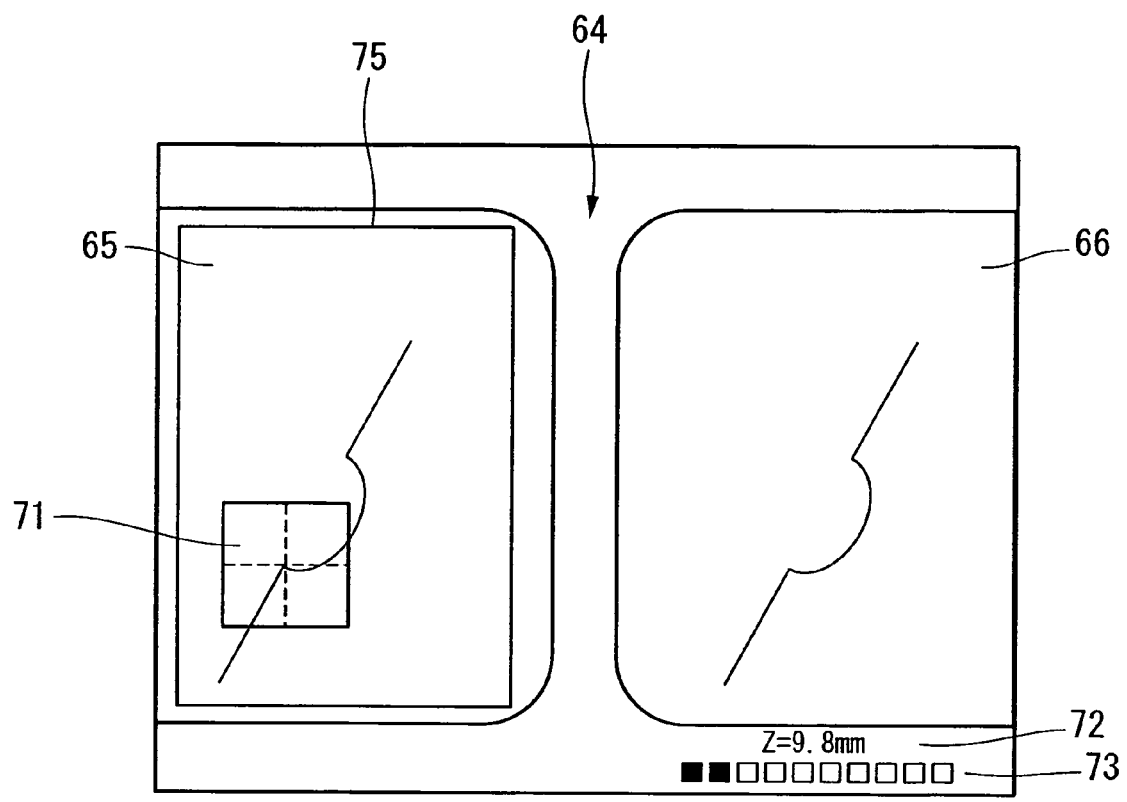
FIG. 12 is a view illustrating first and second images that are displayed on a screen of the main display shown in FIG. 1 in accordance with a second embodiment of the present invention.

FIG. 12 is a view illustrating first and second images that are displayed on a screen of the main display shown in FIG. 1 in accordance with a second embodiment of the present invention. In the above-describe first embodiment, the sight 71 is fixed over the screen 64. In accordance with this embodiment, the sight 71 can be moved by an operator. The operator may operate the lever switch 42 of the remote controller 4 to move the sight 71 in up and down directions as well as in right and left directions. A three dimensional measurable range 75 is also displayed on the screen 64. The distance measuring point is defined by the sight 71. If the distance measuring point is within the three dimensional measurable range 75, thus this means that the distance is measurable. The position of the first image depends on the optical adaptor. The coordinates of the three dimensional measurable range 75 are stored as optical data in the memory card.

Figure 13:
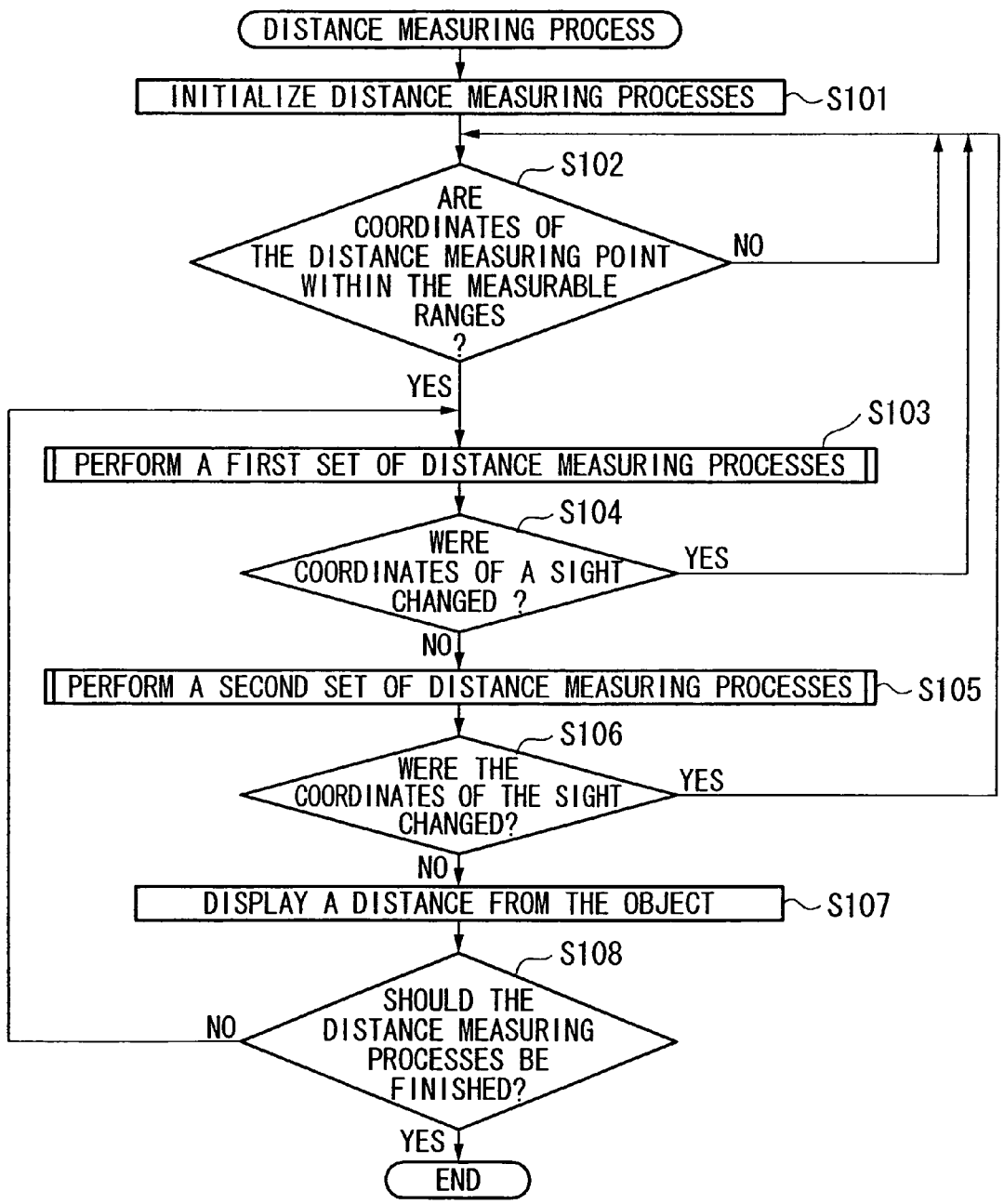
FIG. 13 is a flow chart illustrating the distance measuring process in accordance with the second embodiment of the present invention.
Figure 14:
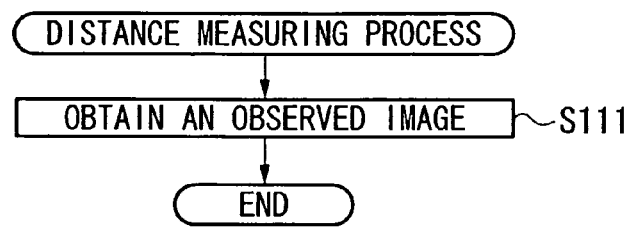
FIG. 14 is a flow chart illustrating the first distance measuring process in Step S103 shown in FIG. 13.

FIG. 13 is a flow chart illustrating the distance measuring process in accordance with the second embodiment of the present invention. In Step S101, an initialization is made of the distance measuring processes. In Step S102, a determination is made of whether or not coordinates of the distance measuring point are within the three dimensional measurable range 75. A first distance measuring process is performed in Step S103 after it has been confirmed that the coordinates of the distance measuring point are within the three dimensional measurable range 75. The performance of the first distance measuring process is waiting until it has been confirmed that the coordinates of the distance measuring point are within the three dimensional measurable range 75. FIG. 14 is a flow chart illustrating the first distance measuring process in Step S103 shown in FIG. 13. The distance measuring process of Step S103 includes a process of Step S111 shown in FIG. 14. In Step S111, the observed image is obtained to develop the obtained image over the memory.

In Step S104, a determination is made of whether or not coordinates of the sight 71 have been changed. If the coordinates of the sight 71 have been changed, then the process flow will return to Step S102 so that the determination is again made of whether or not coordinates of the distance measuring point are within the three dimensional measurable range 75.

Figure 15:
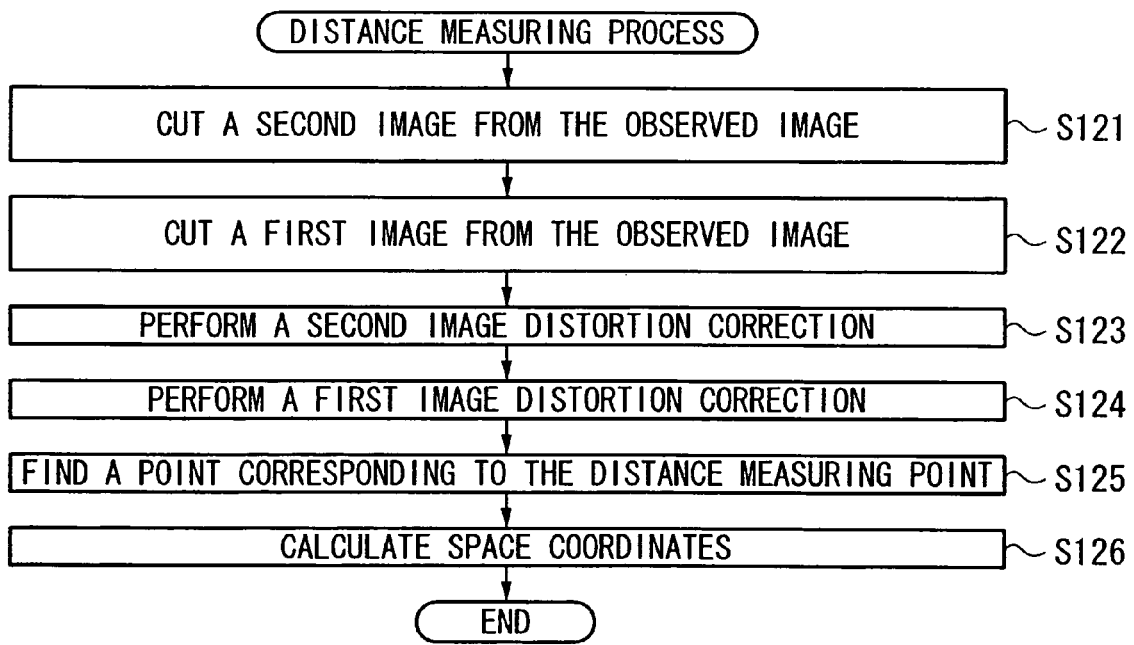
FIG. 15 is a flow chart illustrating the second distance measuring process in Step S105 shown in FIG. 13.

If it has been confirmed that the coordinates of the sight 71 remain unchanged, the process flow will enter into Step S105, in which a second distance measuring process is performed. FIG. 15 is a flow chart illustrating the second distance measuring process in Step S105 shown in FIG. 13. The second distance measuring process of Step S105 includes processes shown in FIG. 15. In Step S121, the second image 66 is cut from the observed image. In Step S122, the first image 65 is cut from the observed image. In Step S123, a correction is made to a distortion of the second image 66. In Step S124, another correction is made to another distortion of the first image 65. In Step S125, a point corresponding to the distance measuring point is found, wherein the distance measuring point is included in the first image 65 and the corresponding point is included in the second mage 66. In Step S126, space coordinates are calculated based on the principle of triangulation. The calculation is made with reference to a length L and a focal distance of the optical system and also to coordinates of the first and second focusing points $Q_L$ and $Q_R$. The distance or length L between the first and second principal points OL and OR of the optical system and the focal length thereof have previously been recorded as optical data in the memory card. A distance to the distance measuring point is found using the calculated space coordinates.

With reference back to FIG. 13, the second distance measuring process has been completed which includes Steps S121 through S126, the process flow will enter into Step S106, in which a determination is made of whether or not coordinates of the sight 71 have been changed. If the coordinates of the sight 71 have been changed, then the process flow will return to Step S102 so that the determination is again made of whether or not coordinates of the distance measuring point are within the three dimensional measurable range 75. The first distance measuring process is performed in Step S103 after it has been confirmed that the coordinates of the distance measuring point are within the three dimensional measurable range 75. The performance of the first distance measuring process is waiting until it has been confirmed that the coordinates of the distance measuring point are within the three dimensional measurable range 75.

If it has been confirmed that the coordinates of the sight 71 remain unchanged, the process flow will enter into Step S107, in which the distance to an object is displayed on the screen 64 of the LCD 5.

In Step S108, a determination is made of whether a distance measuring display finishing operation has been performed. If the distance measuring display finishing operation has not yet been performed, then the process flow will return to the above Step S103, and the distance measuring process will continue. The distance to the object is displayed in real time together with the live image or the freeze image. If the distance measuring display finishing operation has been performed, then the distance measuring process has been completed and finished.

If the object to be measured is positioned near the edge of the screen, the operator may operate the lever switch 42 to move the sight 71 onto the object.

In each of Steps S104 and S106, the determination is made of whether or not the coordinates of the sigh mark 71 have been changed because the process for obtaining the observed image and the process for obtaining the space coordinates take times during which the sight 71 may be moved.

Third Embodiment

Figure 16:
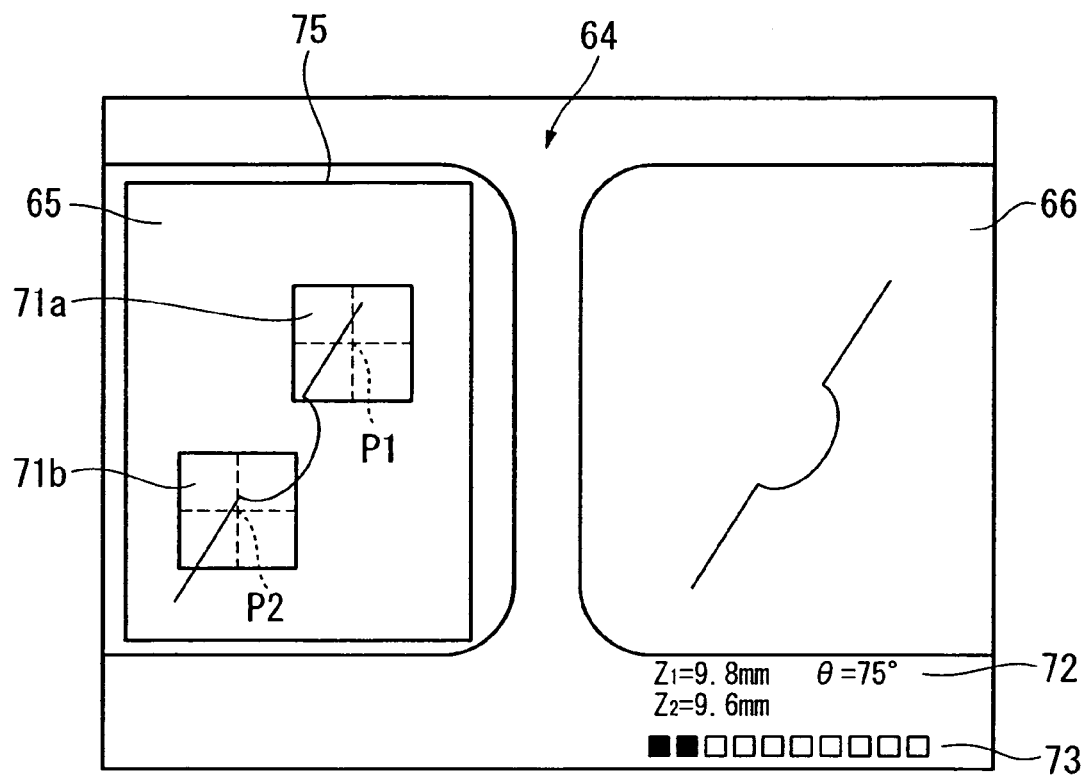
FIG. 16 is a view illustrating first and second images that are displayed on a screen of the main display shown in FIG. 1 in accordance with a third embodiment of the present invention.

FIG. 16 is a view illustrating first and second images that are displayed on a screen of the LCD shown in FIG. 1 in accordance with a third embodiment of the present invention. In the above-described first and second embodiments, the single sight 71 is used. In this embodiment, first and second sights 71a and 71b are used in order to recognize space coordinates of two distance measuring points. An angle can be found of the object with reference to a straight line that is defined between the two distance measuring points. A determination is made of whether or not a front view of the object is obtained, wherein the determination is made with reference to the angle.

The first sight 71a corresponds to a first distance measuring point P1 that has first coordinates (x1, y1, z1). The second sight 71b corresponds to a second distance measuring point P2 that has second coordinates (x2, y2, z2). A unit vector PV of a straight line that connects the first and second distance measuring points P1 and P2 is defined as PV=(P2−P1)/(|P2−P1|). A line of sight Q is given as Q=(0, 0, 1). An angle θ between PV and Q is given as θ=ArcCos(PV·Q), where PV·Q is the inner product of PV and Q, and ArcCos (x) means the arccosine of x. As described above, the angle between the straight line and the line of sight can be found from the first coordinates and the second coordinates. The straight line connects the first and second distance measuring points P1 and P2. The first coordinates belong to the first distance measuring point P1 that corresponds to the first sight 71a. The second coordinates belong to the second distance measuring point P2 that corresponds to the second sight 71b.

Figure 17:
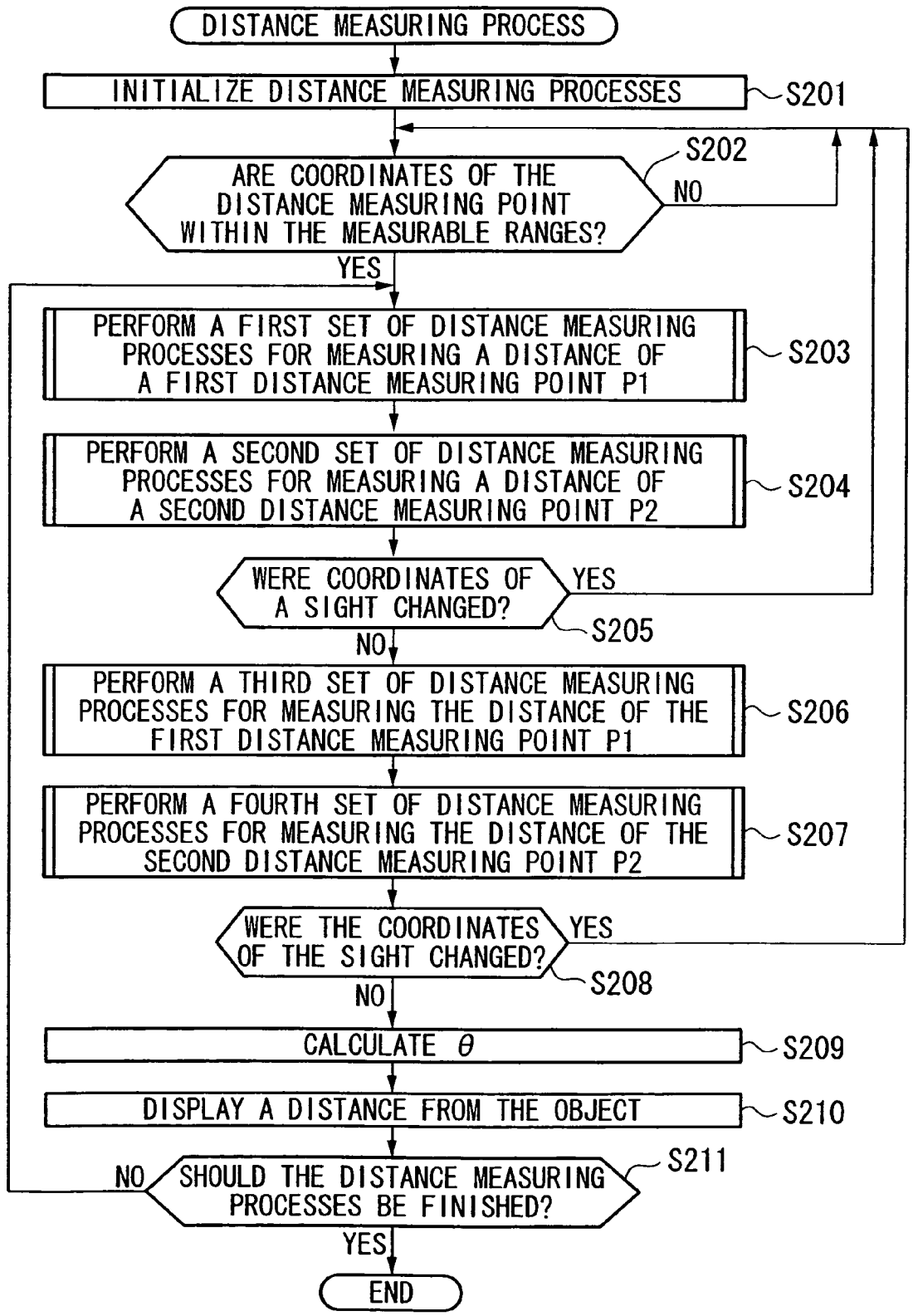
FIG. 17 is a flow chart illustrating the distance measuring process in accordance with the third embodiment of the present invention.

FIG. 17 is a flow chart illustrating distance measuring processes in accordance with the third embodiment of the present invention. In Step S201, an initialization is made of the distance measuring processes. In Step S202, a determination is made of whether or not coordinates of first and second distance measuring point are within a predetermined three dimensional measurable range. A first distance measuring process for the first distance measuring point is performed in Step S203 after it has been confirmed that the coordinates of the first distance measuring point are within the three dimensional measurable range. The performance of the first distance measuring process is waiting until it has been confirmed that the coordinates of the first distance measuring point are within the three dimensional measurable range.

A second distance measuring process for the second distance measuring point is performed in Step S204 after it has been confirmed that the coordinates of the second distance measuring point are within the three dimensional measurable range. The performance of the second distance measuring process is waiting until it has been confirmed that the coordinates of the second distance measuring point are within the three dimensional measurable range. Each of the first and second distance measuring processes in Steps S203 and S204 is substantially the same as that of Step S111 shown in FIG. 14.

In Step S205, a determination is made of whether or not coordinates of the first and second sights 71a and 71b have been changed. If the coordinates of the first and second sights 71a and 71b have been changed, then the process flow will return to Step S202 so that the determination is again made of whether or not coordinates of the first and second distance measuring points are within the three dimensional measurable range. If it has been confirmed that the coordinates of the first and second sights 71a and 71b remain unchanged, the process flow will enter into Steps S206 and S207. In Step 206, a third distance measuring process is performed for the first distance measuring point. In Step 207, a fourth distance measuring process is performed for the second distance measuring point. Each of the third and fourth distance measuring processes in Steps S206 and S207 is substantially the same as those of Steps S121 through S126 shown in FIG. 15.

In Step S208, a determination is made of whether or not coordinates of the first and second sights 71a and 71b have been changed. If the coordinates of the first and second sights 71a and 71b have been changed, then the process flow will return to Step S202 so that the determination is again made of whether or not coordinates of the first and second distance measuring points are within the three dimensional measurable range.

If it has been confirmed that the coordinates of the first and second sights 71a and 71b remain unchanged, the process flow will enter into Step S209, in which a calculation is made of the angle θ between the straight line and the line of sight. The straight line connects the first and second distance measuring points. The first distance measuring point corresponds to the first sight 71a. The second distance measuring point corresponds to the second sight 71b. In Step S210, the first and second distances to the first and second distance measuring points and the angle θ are displayed on the screen 64 of the LCD 5.

In Step S211, a determination is made of whether a distance measuring display finishing operation has been performed. If the distance measuring display finishing operation has not yet been performed, then the process flow will return to the above Step S203, and the distance measuring processes for the first and second distance measuring points will continue. The first and second distances to the first and second distance measuring points and the angle θ are displayed in real time together with the live image or the freeze image. If the distance measuring display finishing operation has been performed, then the distance measuring process has been completed and finished.

In this embodiment, the first and second sights 71a and 71b are used to perform first and second distance measuring processes at the first and second distance measuring points so that the distances to the first and second distance measuring points and the angle are displayed. The angle is defined between the straight line that connects the first and second distance measuring points and the line of sight. An operator may adjust the direction of a camera so that the angle comes close to 90 degrees, while monitoring the angle between the straight line that connects the first and second distance measuring points and the line of sight. The angle being 90 degrees means that the front view of the object is obtained.

Fourth Embodiment

Figure 18:
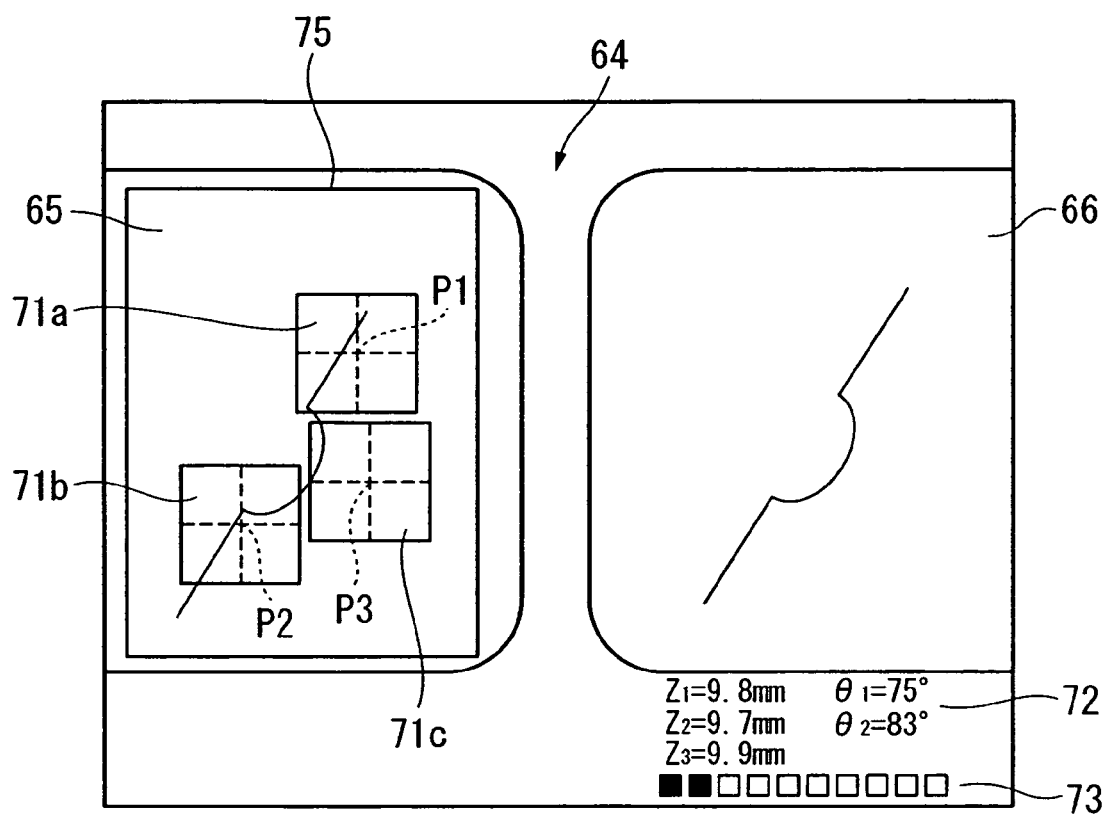
FIG. 18 is a view illustrating first and second images that are displayed on a screen of the main display shown in FIG. 1 in accordance with a fourth embodiment of the present invention.

FIG. 18 is a view illustrating first and second images that are displayed on a screen of the main display shown in FIG. 1 in accordance with a fourth embodiment of the present invention. In the above-described third embodiments, the first and second sights 71a and 71b are used. In this embodiment, first, second and third sights 71a, 71b and 71c are used in order to recognize space coordinates of three distance measuring points. First, second and third distance measuring points are given, which correspond to the first, second and third sights 71a, 71b and 71c, respectively. Three sets of space coordinates are defined by the three sights. A first straight line is defined, which connects the first and second distance measuring points. A second straight line is defined, which connects the second and third distance measuring points. A first angle is defined between the first straight line and a line of sight. A second angle is also defined between the second straight line and the line of sight. A highly accurate determination of whether the front view of the observed object is obtained can be made with reference to the first and second angles.

The first sight 71a corresponds to a first distance measuring point P1 that has first coordinates (x1, y1, z1). The second sight 71b corresponds to a second distance measuring point P2 that has second coordinates (x2, y2, z2). The third sight 71c corresponds to a third distance measuring point P3 that has third coordinates (x3, y3, z3).

A first unit vector PV1 of a first straight line L1 that connects the first and second distance measuring points P1 and P2 is defined as PV1=(P2−P1)/(|P2−P1|). A line of sight Q is given as Q=(0, 0, 1). A first angle θ1 between PV1 and Q is given as θ1=ArcCos(PV1·Q), where PV1·Q is the inner product of PV1 and Q, and ArcCos (x) means the arccosine of x. As described above, the first angle between the first straight line and the line of sight can be found from the first coordinates and the second coordinates. The first straight line connects the first and second distance measuring points P1 and P2. The first coordinates belong to the first distance measuring point P1 that corresponds to the first sight 71a. The second coordinates belong to the second distance measuring point P2 that corresponds to the second sight 71b.

A second unit vector PV2 of a second straight line L2 that connects the second and third distance measuring points P2 and P3 is defined as PV2=(P3−P2)/(|P3−P2|). The line of sight Q is given as Q=(0, 0, 1). A second angle θ2 between PV2 and Q is given as θ2=ArcCos(PV2·Q), where PV2·Q is the inner product of PV2 and Q, and ArcCos (x) means the arccosine of x. As described above, the second angle between the second straight line and the line of sight can be found from the second coordinates and the third coordinates. The second straight line connects the second and third distance measuring points P2 and P3. The second coordinates belong to the second distance measuring point P2 that corresponds to the second sight 71b. The third coordinates belong to the third distance measuring point P3 that corresponds to the third sight 71c.

The second angle θ2 can also be found as follows. The second straight line is newly defined to be a straight line that connects the third distance measuring point P3 and a crossing point P4. The crossing point P4 is defined by the straight line L1 and a normal line. The normal line is the normal to the first straight line L1. The normal line further includes the third distance measuring point P3. The second unit vector PV2 is newly defined as PV2=(P3−P4)/(|P3−P4|). The crossing point P4 can be given by P4=P1*t+P1, t=P1·(P3−P1)/(|P2−P1|), where "t" is a parameter.

Figure 19:
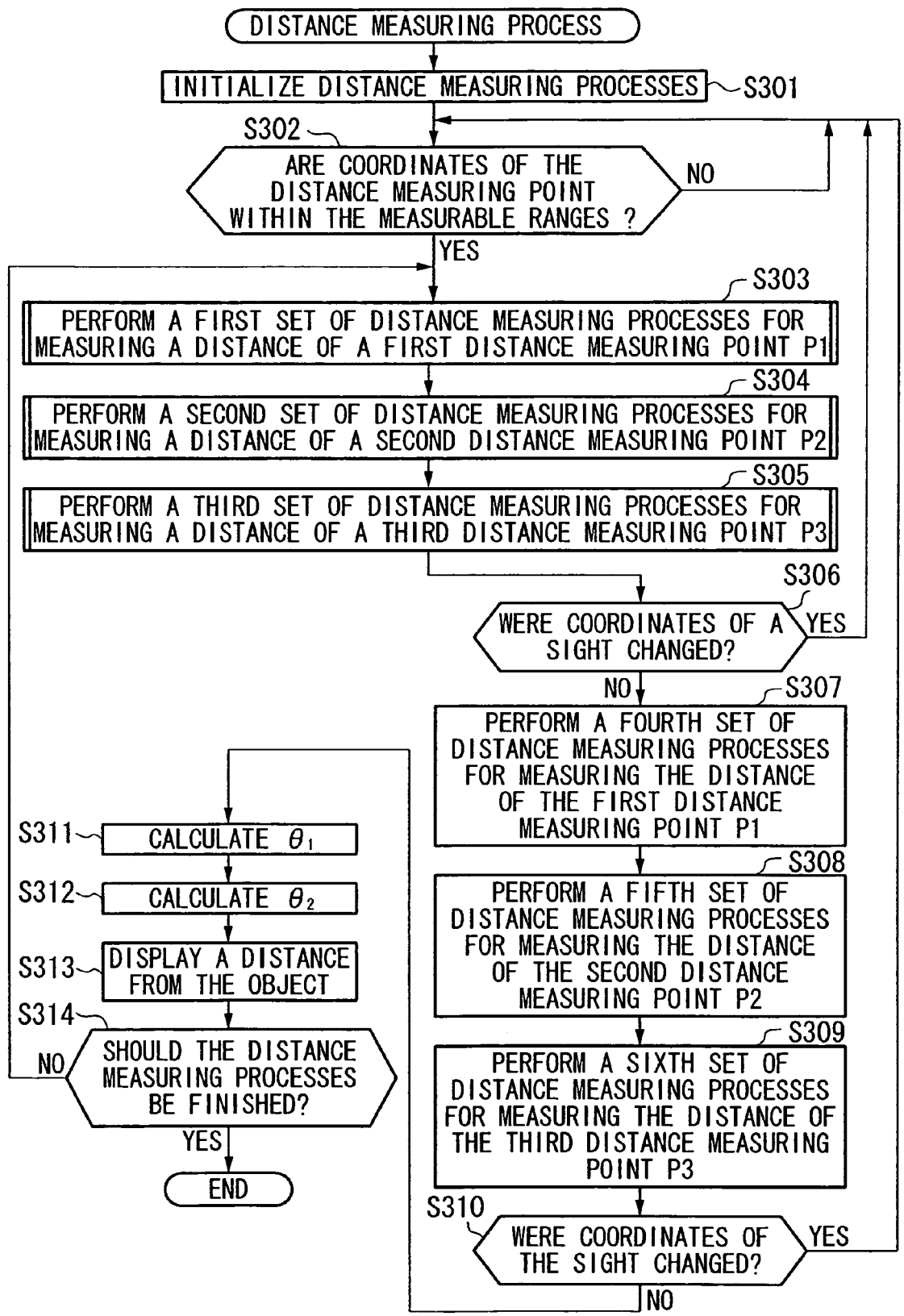
FIG. 19 is a flow chart illustrating distance measuring processes in accordance with the fourth embodiment of the present invention.

FIG. 19 is a flow chart illustrating distance measuring processes in accordance with the fourth embodiment of the present invention. In Step S301, an initialization is made of the distance measuring processes. In Step S302, a determination is made of whether or not coordinates of first and second distance measuring point are within a predetermined three dimensional measurable range. A first distance measuring process for the first distance measuring point is performed in Step S303 after it has been confirmed that the coordinates of the first distance measuring point are within the three dimensional measurable range. The performance of the first distance measuring process is waiting until it has been confirmed that the coordinates of the first distance measuring point are within the three dimensional measurable range. A second distance measuring process for the second distance measuring point is performed in Step S304 after it has been confirmed that the coordinates of the second distance measuring point are within the three dimensional measurable range. The performance of the second distance measuring process is waiting until it has been confirmed that the coordinates of the second distance measuring point are within the three dimensional measurable range. A third distance measuring process for the third distance measuring point is performed in Step S305 after it has been confirmed that the coordinates of the third distance measuring point are within the three dimensional measurable range. The performance of the third distance measuring process is waiting until it has been confirmed that the coordinates of the third distance measuring point are within the three dimensional measurable range. Each of the first, second and third distance measuring processes in Steps S303, S304 and S305 is substantially the same as that of Step S111 shown in FIG. 14.

In Step S306, a determination is made of whether or not coordinates of the first, second and third sights 71a, 71b and 71c have been changed. If the coordinates of the first, second and third sights 71a, 71b and 71c have been changed, then the process flow will return to Step S302 so that the determination is again made of whether or not coordinates of the first, second and third distance measuring points are within the three dimensional measurable range. If it has been confirmed that the coordinates of the first, second and third sights 71a, 71b and 71c remain unchanged, the process flow will enter into Steps S307, S308 and S309. In Step S307, a fourth distance measuring process is performed for the first distance measuring point. In Step S308, a fifth distance measuring process is performed for the second distance measuring point. In Step S309, a sixth distance measuring process is performed for the third distance measuring point. Each of the fourth, fifth and sixth distance measuring processes in Steps S307, S308 and S309 is substantially the same as those of Steps S121 through S126 shown in FIG. 15.

In Step S310, a determination is made of whether or not coordinates of the first, second and third sights 71a, 71b and 71c have been changed. If the coordinates of the first, second and third sights 71a, 71b and 71c have been changed, then the process flow will return to Step S302 so that the determination is again made of whether or not coordinates of the first, second and third distance measuring points are within the three dimensional measurable range.

If it has been confirmed that the coordinates of the first, second and third sights 71a, 71b and 71c remain unchanged, the process flow will enter into Steps S311 and S312. In Step S311, a first calculation is made of the first angle θ1 between the first straight line and the line of sight. In Step S312, a second calculation is made of the second angle θ2 between the second straight line and the line of sight. The first straight line connects the first and second distance measuring points. The first distance measuring point corresponds to the first sight 71a. The second distance measuring point corresponds to the second sight 71b. The second straight line connects the second and third distance measuring points. The third distance measuring point corresponds to the third sight 71c. In Step S313, the first, second and third distances to the first, second and third distance measuring points and the first and second angles θ1 and θ2 are displayed on the screen 64 of the LCD 5.

In Step S314, a determination is made of whether a distance measuring display finishing operation has been performed. If the distance measuring display finishing operation has not yet been performed, then the process flow will return to the above Step S303, and the distance measuring processes for the first, second and third distance measuring points will continue. The first, second and third distances to the first, second and third distance measuring points and the first and second angles θ1 and θ2 are displayed in real time together with the live image or the freeze image. If the distance measuring display finishing operation has been performed, then the distance measuring process has been completed and finished.

The distance to the object is displayed in real time together with the live image. The depth of field is deep. It is difficult to estimate the object distance from a focus in the field of view. A camera enters into the field of observation, and thus it is difficult to estimate the positional relationship between the camera and the object. Notwithstanding, an operator can recognize the distance to the observed object, the distance being displayed on the display screen together with the live image. The operator can determine whether or not the highly accurate three dimensional measurement image is obtainable. The three dimensional measurement process will be started until the camera comes close to the object so that the highly accurate three dimensional measurement is obtainable.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A measuring endoscope apparatus comprising:
   a stereo optical endoscope that provides a plurality of observation fields from one position of the head of the stereo optical endoscope, the stereo optical endoscope comprising an image pickup unit;
   an image processing unit that receives an image pickup signal from the image pickup unit, the image processing unit generating an image signal from the image pickup signal;
   a control unit comprising a measurement processing unit, the measurement processing unit receiving the image signal from the image processing unit, the measurement processing unit performing a measurement process based on the image signal;
   a display unit that receives an output image from the control unit, the display unit displaying the output image;
   an observation image capturing unit that captures an observation image of an object;
   a distance measuring processing unit that calculates an object distance from a distance measuring point designated on the observation image to an image pickup surface of the image pickup unit, the calculation being made based on the observation image that is captured at a time; and
   a measurable range display unit that displays an indication related to the object distance.

2. The measuring endoscope apparatus according to claim 1, further comprising:
   a sight position changing unit that changes a position of the sight; and
   a sight-coordinate setting unit that sets coordinates of the sight.

3. The measuring endoscope apparatus according to claim 1, further comprising:
   a determination unit that determines whether or not the object distance is within a measurable range, wherein the measurable range display unit displays the indication in accordance with a result of the determination concurrently with the observation image.

4. The measuring endoscope apparatus according to claim 3, wherein the determination unit sends the control unit the result of the determination to allow the control unit to control the measurement processing unit to start performing the measurement process when the object distance is within the measurable range.

5. The measuring endoscope apparatus according to claim 3, wherein the measurable range display unit displays a bar graph representing the object distance.

6. The measuring endoscope apparatus according to claim 1, wherein the measurable range display unit numerically displays the indication concurrently with the observation image.

7. The measuring endoscope apparatus according to claim 1, wherein the head of the stereo optical endoscope has a plurality of stereo optical adaptors that provide the plurality of observation fields.

8. The measuring endoscope apparatus according to claim 1, wherein the object distance is a distance from the image pickup unit to a location on the object designated by the distance measuring point.

9. The measuring endoscope apparatus according to claim 1, further comprising:
   a sight display unit that displays a sight at coordinates that are positioned on the observation image, the sight representing the distance measuring point, the sight being superimposed on the observation image.

10. A program to be executed for performing operations of an endoscope apparatus comprising: a stereo optical endoscope comprising an image pickup unit; an image processing unit that receives an image pickup signal from the image pickup unit, the image processing unit generating an image signal from the image pickup signal; a control unit comprising a measurement processing unit, the measurement processing unit receiving the image signal from the image processing unit, the measurement processing unit performing a measurement process based on the image signal; a display unit that receives an output image from the control unit, the display unit displaying the output image, the program comprising:
    capturing an observation image of an object, while allowing the stereo optical endoscope to provide a plurality of observation fields from one position of the head of the stereo optical endoscope;
    calculating an object distance from a distance measuring point designated on the observation image to an image pickup surface of the image pickup unit, the calculation being made based on the observation image that is captured at a time; and
    displaying an indication related to the object distance.

11. The program according to claim 10, further comprising:
    changing a position of the sight; and
    setting coordinates of the sight.

12. The program according to claim 10, further comprising:
    determining whether or not the object distance is within a measurable range, wherein the indication is displayed in accordance with a result of the determination concurrently with the observation image.

13. The program according to claim 12, wherein the result of the determination is used to allow the control unit to control the measurement processing unit to start performing the measurement process when the object distance is within the measurable range.

14. The program according to claim 12, wherein a bar graph that represents the object distance is displayed.

15. The program according to claim 10, wherein displaying an indication related to the object distance comprises numerically displaying the indication concurrently with the observation image.

16. The program according to claim 10, wherein the head of the stereo optical endoscope has a plurality of stereo optical adaptors that provide the plurality of observation fields.

17. The program according to claim 10, wherein the object distance is a distance from the image pickup unit to a location on the object designated by the distance measuring point.

18. The program according to claim 10, further comprising:
displaying a sight at coordinates that are positioned on the observation image, the sight representing a distance measuring point, the sight being superimposed on the observation image.

19. An endoscope apparatus comprising:
an observation image capturing unit that captures an observation image of an object;
a distance measuring processing unit that calculates an object distance from a distance measuring point designated on the observation image to an image pickup surface of the image pickup unit, the calculation being made based on the observation image that is captured at a time; and
a measurable range display unit that displays an indication related to the object distance.

20. The endoscope apparatus according to claim 19, further comprising:
a determination unit that determines whether or not the object distance is within the measurable range, wherein the measurable range display unit displays the indication in accordance with a result of the determination concurrently with the observation image.

21. The endoscope apparatus according to claim 20, wherein the determination unit sends the control unit the result of the determination to allow the control unit to control the measurement processing unit to start performing the measurement process when the object distance is within the measurable range.

22. The endoscope apparatus according to claim 20, wherein the measurable range display unit displays a bar graph representing the object distance.

23. The endoscope apparatus according to claim 20, wherein the measurable range display unit displays an alert when the object distance is outside the measurable range.

24. The endoscope apparatus according to claim 19, further comprising:
a sight display unit that displays at least one sight, the at least one sight being superimposed on the observation image, the at least one sight representing the distance measuring point.

25. The endoscope apparatus according to claim 24, wherein the sight display unit displays a plurality of sights on the observation image.

26. The endoscope apparatus according to claim 24, further comprising:
a sight position changing unit that changes a position of the at least one sight; and
a sight-coordinate setting unit that sets coordinates of the at least one sight.

27. The endoscope apparatus according to claim 19, further comprising:
a stereo optical endoscope that provides a plurality of observation fields from one position of the head of the stereo optical endoscope, the stereo optical endoscope comprising an image pickup unit.

28. The endoscope apparatus according to claim 19, wherein the measurable range is a three dimensional measurable range.

29. A method of operating an endoscope apparatus, the method comprising:
capturing an observation image of an object;
calculating an object distance from a distance measuring point designated on the observation image to an image pickup surface of the image pickup unit, the calculation being made based on the observation image that is captured at a time; and
displaying an indication related to the object distance.

30. The method according to claim 29, further comprising:
determining whether or not the object distance is within the measurable range, the determination unit generating the set of information,
wherein the indication is displayed in accordance with a result of the determination concurrently with the observation image.

31. The method according to claim 30, wherein the result of the determination is used to allow the control unit to control the measurement processing unit to start performing the measurement process when the object distance is within the measurable range.

32. The method according to claim 30, wherein a bar graph that represents the object distance is displayed.

33. The method according to claim 29, further comprising:
displaying at least one sight, the at least one sight being superimposed on the observation image, the at least one sight representing the distance measuring point.

34. The method according to claim 33, wherein displaying the at least one sight comprises displaying a plurality of sights on the observation image.

35. The method according to claim 33, further comprising:
changing a position of the at least one sight; and
setting coordinates of the at least one sight.

36. The method according to claim 29, further comprising:
displaying an alert when the object distance is outside the measurable range.

37. The method according to claim 29, wherein the measurable range is a three dimensional measurable range.

38. The method according to claim 29, wherein the observation image is captured in a plurality of observation fields from one position of the head of a stereo optical endoscope of the endoscope apparatus.

* * * * *